(12) United States Patent
Fertig et al.

(10) Patent No.: US 7,071,219 B2
(45) Date of Patent: Jul. 4, 2006

(54) MONO-ACYLATED O-PHENYLENDIAMINES DERIVATIVES

(75) Inventors: Georg Fertig, Penzberg (DE); Frank Herting, Penzberg (DE); Manfred Kubbies, Penzberg (DE); Anja Limberg, Munich (DE); Ulrike Reiff, Penzberg (DE); Michael Weidner, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 89 days.

(21) Appl. No.: 10/771,184

(22) Filed: Feb. 3, 2004

(65) Prior Publication Data

US 2004/0162317 A1 Aug. 19, 2004

(51) Int. Cl.
*A61K 31/34* (2006.01)
*C07D 213/74* (2006.01)

(52) U.S. Cl. .................. 514/354; 514/355; 546/316; 546/323

(58) Field of Classification Search ............. 546/314, 546/316, 323; 514/354, 355
See application file for complete search history.

(56) References Cited

U.S. PATENT DOCUMENTS

| 2,680,731 A | 6/1954 | Martin |
| 3,810,910 A | 5/1974 | Meyer et al. |
| 5,137,918 A | 8/1992 | Weiershausen et al. |
| 2003/0013757 A1 | 1/2003 | Sattelkau et al. |

FOREIGN PATENT DOCUMENTS

| DE | 2 062 265 | 5/1972 |
| EP | 242 851 | 10/1987 |
| EP | 847 992 | 6/1998 |
| EP | 974 576 | 1/2000 |
| FR | 2 167 954 | 8/1973 |
| JP | 10 259176 | 9/1998 |
| JP | 11 269140 | 10/1999 |
| JP | 11 269146 | 10/1999 |
| WO | WO 93/21146 | 10/1993 |
| WO | WO 01/38322 | 5/2001 |
| WO | WO 01/70675 | 9/2001 |
| WO | WO 03/011851 | 2/2003 |

OTHER PUBLICATIONS

Koyama et al., Blood, 96, pp. 1490-1495 (2000).
Rastogi et al., Indian J. Chem., Sect.B, 21B pp. 485-487 (1982).
Moll et al., Z. Chem., 17, pp. 132-134 (1977).
Hassan et al., Indian J. Chem., 39B, pp. 764-768 (2000).
Holba et al., Z. Phys. Chem., 262, pp. 445-448 (1981).
Picard, Claude et al, Synthesis, XP001097260, (10), pp. 1471-1478 (2001).

*Primary Examiner*—Bernard Dentz
(74) *Attorney, Agent, or Firm*—George W. Johnston; Patricia S. Rocha-Tramaloni; Brian C. Remy

(57) ABSTRACT

Mono-acylated o-phenylendiamines derivatives of formula A

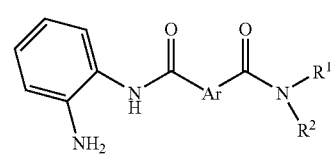

wherein Ar, $R^1$, and $R^2$ are as described herein, have been found useful for the treatment of diseases mediated by the inhibition of histone deacetylase, such as cancer.

39 Claims, No Drawings

MONO-ACYLATED O-PHENYLENDIAMINES DERIVATIVES

BACKGROUND OF THE INVENTION

The present invention generally relates to mono-acylated o-phenylendiamines derivatives and pharmaceutically acceptable salts thereof. The invention also relates to processes for the manufacturing of these compounds of formula I, to pharmaceutical compositions containing such compounds and to their use in the manufacture of drugs for the treatment of diseases such as cancer.

Cancer is one of the major causes of death, exceeding heart and cerebrovascular diseases, and so many studies have been conducted with enormous expense and time to overcome cancer. However, in spite of a variety of therapies such as surgical operation, radiation therapy and chemotherapy, there is still a great need for improved anticancer therapeutics. Among these therapies, chemotherapy is one of the main areas for cancer treatment. Most drugs show their effect by affecting mainly DNA to express their cytotoxicity and then, in consequence injuring tumor cells. However, lacking selectivity, they do not sufficiently differentiate between tumor cells and normal cells, and therefore, adverse reactions expressed in normal cells have limited their use in therapy. Up to now, no satisfactory drugs have been discovered, and thus an anticancer drug with reduced toxicity, better tolerability and a high therapeutic effect is very much desired.

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and induce apoptosis in several types of cancer cells, including colon cancer cells, T-cell lymphoma cells, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490–1495).

EP-A 0 847 992 describes monoacylated o-phenylendiamine derivatives as cell differentiation inducers. The same type of compounds is also the subject of EP-A 0 242 851. The compounds described in these applications are almost exclusively o-phenylene derivatives monoacylated with derivatives of benzoic acid.

Monoacylated o-phenylendiamines are known in the art as precursors for the preparation of the corresponding benzimidazoles, such preparation methods are e.g. described in DE-A 2 062 265; FR 2 167 954; Rastogi, R., and Sharma, S., Indian J. Chem., Sect. B, 21B (5) (1982) 485–487; Moll, R., et al., Z. Chem. 17 (1977) 133–134; and Hassan, H., et al., Indian J. Chem. 39B (2000) 764–768.

As can be seen, there exists a need to provide compounds with improved properties such as increased tolerability, less toxicity and less side effects.

SUMMARY OF THE INVENTION

Broadly, the present invention concerns new compounds of the general formula A

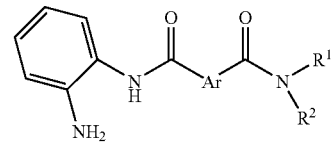

wherein Ar, $R^1$ and $R^2$ are as described hereinbelow.

The compounds according to the present invention are inhibitors of histone deacetylase (HDAC) and therefore exhibit antiproliferative and differentiation-inducing activity, which results in inhibition of tumor cell proliferation, induction of apoptosis and inhibition of invasion. These compounds, therefore, are useful for the treatment of diseases such as cancer in humans or animals. Examples of tumors which may be treated, but are not limited to, colon cancers, breast carcinoma (including advanced breast cancer), lung cancer (e.g. adenocarcinoma and including non-small cell lung cancer), prostate cancer including advanced disease, pancreatic cancers, hematopoetic tumors of lymphoid lineage (e.g. acute lymphotic leukemia, B-cell lymphoma, Burkitt's lymphoma), myeloid leukemias (for example, acute myelogenous leukemia (AML)), thyroid follicular cancer, myelodysplastic syndrome (MSD), tumors of mesenchymal origin, melanomas, teratocarcinomas, neuroblastomas, gliomas, benign tumors of the skin (e.g. keratoacanthomas), kidney carcinoma, ovary carcinoma, bladder carcinoma and epidermal carcinoma.

The compounds of the present invention surprisingly may show low toxicity, together with a potent anti-proliferative and cell differentiation activity characterized by enhanced acetylation due to inhibition of HDAC.

The present invention also encompasses pharmaceutically acceptable salts or prodrugs of the compounds of formula A or formula I as well as the use of these compounds, salts and prodrugs to produce pharmaceutical preparations.

DETAILED DESCRIPTION OF THE INVENTION

The following definitions of the general terms used in the present description apply irrespective of whether the terms in question appear alone or in combination.

The term "$C_1$–$C_{12}$-alkyl" denotes a saturated straight- or branched-chain alkyl group containing from 1 to 12 carbon atoms, for example, methyl, ethyl, propyl, isopropyl, n-butyl, i-butyl, 2-butyl, t-butyl, pentyl, hexyl, heptyl and the like. The term "$C_1$–$C_6$ alkyl" denotes a saturated straight- or branched-chain alkyl group containing from 1 to 6 carbon atoms. The alkyl group may optionally be mono or multiple substituted by hydroxy, halogen, $C_{3\text{-}12}$-cycloalkyl, alkoxy, alkylsulfanyl, acyloxy, alkoxycarbonyl, acyl, $C_{1\text{-}6}$-alkyl-NH—C(O)—, $C_{1\text{-}6}$-alkyl-C(O)NH— or —$NR^3R^4$.

Examples of substituted alkyl residues are for example trifluoromethyl, pentafluoroethyl, 2-dimethylamino-ethyl, 2-diethylamino-ethyl, 2-dibutylamino-ethyl, 2-diisopropylamino-ethyl, 2-methoxy-ethyl, 2-ethoxy-ethyl, 2-propyloxy-ethyl, 3-dimethylamino-propyl, 3-diethylamino-propyl, 3-dibutylamino-propyl, 3-diisopropylamino-propyl, 3-methoxy-propyl, 3-ethoxy-propyl, 3-propyloxy-propyl, 2-acetylamino-ethyl, 3-acetylamino-proyl, 2-methoxy-1-methyl-ethyl (in its (R), (S) and (R,S) form), cyclopropylmethyl, 3-dimethylamino-2,2-dimethylpropyl, 3-(2-oxopyrrolidin-1-yl)-propyl or 2-(2-oxo-pyrrolidin-1-yl)-ethyl.

The term "alkoxy" denotes a group wherein the alkyl residue is as defined above, and which is attached via an oxygen atom.

The term "alkylsulfanyl" denotes a group wherein alkyl residue is as defined above, and which is attached via an sulfur atom.

The term "acyloxy" denotes a group alkyl-C(O)—O—, wherein alkyl residue is as defined above.

The term "alkoxycarbonyl" denotes a group alkyl-O—C(O)—, wherein alkyl residue is as defined above.

The term "acyl" denotes a group alkyl-C(O)—, wherein alkyl residue is as defined above.

The term "$C_2$–$C_{12}$-alkenyl" refers to an unsaturated alkyl group having 2 to 12 carbon atoms and at least one double bond, preferably allyl or pentadienyl.

The term "$C_2$–$C_{12}$-alkynyl" refers to an unsaturated alkyl group having 2 to 12 carbon atoms and at least one triple bond, such as prop-2-ynyl, preferably propargyl.

The term "$C_2$–$C_{12}$-alkenyloxy" denotes a group wherein the alkenyl residue is as defined above, and which is attached via an oxygen atom, preferably allyloxy.

The term "$C_3$–$C_{12}$-cycloalkyl" as used in the present invention denotes saturated carbocyclic rings with 3 to 12 carbon atoms, such as cyclopropyl, cyclobutyl, cyclopentyl, cyclohexyl, cycloheptyl and cyclooctyl.

The term "together with the nitrogen-atom to which they are attached form a ring, which ring is monosubstituted by oxo and which ring may contain a further heteroatom" refers to heterocycles such as pyrrolidinone-1-yl or piperidinone-1-yl.

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid, cyclohexanesulfamic acid and the like.

The term "substituted," as in a substituted alkyl, means that the substitution can occur at one or more positions, and, unless otherwise indicated, that the substituents at each substitution site are independently selected from the specified options.

The term "therapeutically effective amount" means an amount of at least one compound of formula I, or a pharmaceutically acceptable salt thereof, that significantly inhibits proliferation and/or prevents differentiation of a human tumor cell, including human tumor cell lines.

The present invention concerns new compounds of the general formula A

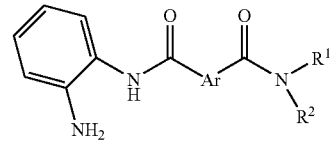

wherein

Ar is thiophen-2,5-diyl, pyridine-2,5-diyl, pyridine-5,2-diyl, pyridine-2,6-diyl, pyridine-2,4-diyl or 1,4-phenylene, $R^1$, $R^2$ are independently selected from hydrogen, substituted or unsubstituted $C_{1-12}$-alkyl, substituted or unsubstituted $C_{2-12}$-alkenyl, substituted or unsubstituted $C_{2-12}$-alkynyl, and substituted or unsubstituted $C_{3-12}$-cycloalkyl, wherein the substituent is selected from hydroxy, halogen, $C_{3-12}$-cycloalkyl, alkoxy, alkylsulfanyl, acyloxy, alkoxycarbonyl, acyl, $C_{1-6}$-alkyl-NH—C(O)—, $C_{1-6}$-alkyl-C(O)NH— and —$NR^3R^4$, or alternatively $R^1$ is hydrogen, and $R^2$ is hydroxyl, alkoxy, $C_2$–$C_{12}$-alkenyloxy, phenoxy, or substituted phenoxy, wherein the substituent is selected from methyl, methoxy, halogen, nitro, cyano, trifluoromethyl, ethenyl and —C(O)—O—$CH_3$, provided that if $R^2$ is hydroxy, Ar is not thiophen-2,5-diyl; and $R^3$ and $R^4$ are each independently selected from hydrogen or $C_{1-6}$-alkyl, or wherein $R^3$ and $R^4$ together with the nitrogen-atom to which they are attached form a ring, which ring is monosubstituted by oxo and which ring may contain a further heteroatom, or a pharmaceutically acceptable salt thereof.

Especially preferred are the compounds of formula I

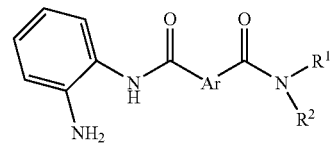

wherein

Ar is thiophen-2,5-diyl, pyridine-2,5-diyl, pyridine-5,2-diyl or 1,4-phenylene, $R^1$, $R^2$ are each independently selected from the group hydrogen, substituted or unsubstituted $C_{1-12}$-alkyl, substituted or unsubstituted $C_{2-12}$-alkenyl, substituted or unsubstituted $C_{2-12}$-alkynyl, and substituted or unsubstituted $C_{3-12}$-cycloalkyl, wherein the substituent is selected from hydroxy, halogen, $C_{3-12}$-cycloalkyl, alkoxy, alkylsulfanyl, acyloxy, alkoxycarbonyl, acyl, $C_{1-6}$-alkyl-NH—C(O)—, $C_{1-6}$-alkyl-C(O)NH— and —$NR^3R^4$, $R^3$ and $R^4$ are each independently selected from hydrogen or $C_{1-6}$-alkyl, or wherein $R^3$ and $R^4$ together with the nitrogen-atom to which they are attached form a ring, which ring is monosubstituted by oxo and which ring may contain a further heteroatom, or a pharmaceutically acceptable salt thereof.

Compounds of the present invention can contain one or several chiral centres and can then be present in a racemic or in an optically active form. The racemates can be separated according to known methods into the enantiomers. Preferably diastereomeric salts which can be separated by crystallization are formed from the racemic mixtures by reaction with an optically active acid such as e.g. D- or L-tartaric acid, mandelic acid, malic acid, lactic acid or camphorsulfonic acid. Furthermore, the racemic compounds can be separated into their enantiomers by chromatography on an analytical, semipreparative or preparative scale using suitable optically active stationary phases with suitable eluents. Suitable optically active stationary phases include, but are not limited to, silica (e.g. ChiraSper,Merck; Chiralpak OT/OP, Baker), cellulose esters or carbamates (e.g. Chiracel OB/OY, Baker) or others (e.g. Crownpak, Daicel or Chiracel OJ-R, Baker).

Enantiomers, diastereoisomers and racemates of formula A or I and their pharmaceutically acceptable salts are also part of the invention.

Preferred groups of compounds of formula I or A are as follows:

(1) compounds, wherein $R^1$ is hydrogen or alkyl, and $R^2$ is hydrogen, $C_{1-12}$-alkyl, $C_{2-12}$-alkenyl, $C_{2-12}$-alkynyl, the alkyl, alkenyl and alkynyl groups being optionally mono or multiple substituted by hydroxy, halogen, alkoxy, alkylsulfanyl, acyloxy, alkoxycarbonyl, acyl, $C_{1-6}$-alkyl-NH—C(O)—, $C_{1-6}$-alkyl-C(O)NH— or —$NR^3R^4$; wherein $R^3R^4$ are as defined above;

(2) compounds of formula I or A, wherein $R^1$ is hydrogen and $R^2$ is alkenyl or alkynyl; compounds, wherein $R^1$ is hydrogen and $R^2$ is unsubstituted straight or branched $C_{1-12}$-alkyl or alkyl mono or multiple substituted by alkoxy, alkylsulfanyl, acyloxy, alkoxycarbonyl, acyl, $C_{1-6}$-alkyl-NH—C(O)—, or $C_{1-6}$-alkyl-C(O)NH—;

(3) compounds of formula I or A, wherein $R^1$ is hydrogen and $R^2$ is $C_{1-12}$-alkyl mono or multiple substituted by —$NR^3R^4$, wherein $R^3$ and $R^4$ independently from each other represent hydrogen or $C_{1-6}$-alkyl; and (4) compounds of formula I or A according to claim 1, wherein $R^1$ is hydrogen and $R^2$ is alkyl mono or multiple substituted by —$NR^3R^4$, wherein $R^3$ and $R^4$ together with the nitrogen-atom to which they are attached form a ring, which ring is monosubstituted by oxo and which ring may contain a further heteroatom.

Preferred are the compounds of formula I, wherein Ar is thiophen-2,5-diyl of the formula I-A

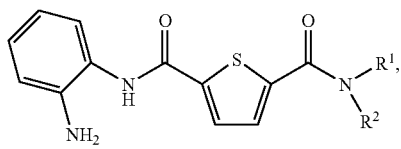

I-A wherein $R^1$ is hydrogen or $C_{1-6}$-alkyl; and $R^2$ is hydrogen, $C_{1-12}$-alkyl, $C_{2-12}$-alkenyl, $C_{2-12}$-alkynyl, the alkyl, alkenyl and alkynyl groups being optionally mono or multiple substituted by hydroxy, halogen, alkoxy, alkylsulfanyl, acyloxy, alkoxycarbonyl, acyl, $C_{1-6}$-alkyl-NH—C(O)—, $C_{1-6}$-alkyl-C(O)NH— or —$NR^3R^4$; wherein $R^3R^4$ are as defined above.

Examples of such compounds are ex. no. Compound
1-19 thiophene-2,5-dicarboxylic acid 2-[(2-amino-phenyl)-amide]5-(butyl-methyl-amide),
1-34 thiophene-2,5-dicarboxylic acid 2-[(2-amino-phenyl)-amide]5-diethylamide,
1-36 Thiophene-2,5-dicarboxylic acid 2-[(2-amino-phenyl)-amide]5-(methyl-prop-2-ynyl-amide),
1-37 thiophene-2,5-dicarboxylic acid 2-(allyl-methyl-amide) 5-[(2-amino-phenyl)-amide],
1-38 thiophene-2,5-dicarboxylic acid 2-[(2-amino-phenyl)-amide]5-[(2-dimethylaminoethyl)-ethyl-amide],
1-39 thiophene-2,5-dicarboxylic acid 2-[(2-amino-phenyl)-amide]5-dipropylamide,
1-40 thiophene-2,5-dicarboxylic acid 2-[(2-amino-phenyl)-amide]5-(methyl-pentyl-amide),
1-41 thiophene-2,5-dicarboxylic acid 2-[(2-amino-phenyl)-amide]5-[(2-diethylaminoethyl)-methyl-amide],
1-42 thiophene-2,5-dicarboxylic acid 2-[(2-amino-phenyl)-amide]5-[bis-(2-methoxy-ethyl)-amide],
1-44 thiophene-2,5-dicarboxylic acid 2-amide 5-[(2-amino-phenyl)-amide].

Further preferred are the compounds of formula I or A or I-A, wherein $R^1$ is hydrogen and $R^2$ is alkenyl or alkynyl. Such compounds are for example ex. no. Compound
1-30- thiophene-2,5-dicarboxylic acid 2-[(2-amino-phenyl)-amide]5-prop-2-ynylamide,
1-32 thiophene-2,5-dicarboxylic acid 2-allylamide 5-[(2-amino-phenyl)-amide].

Further preferred are compounds of formula I or A or I-A, wherein $R^1$ is hydrogen and $R^2$ is unsubstituted straight or branched $C_{1-12}$-alkyl or alkyl mono or multiple substituted by alkoxy, alkylsulfanyl, acyloxy, alkoxycarbonyl, acyl, $C_{1-6}$-alkyl-NH—C(O)—, or $C_{1-6}$-alkyl-C(O)NH—.

Examples of such compounds are ex. no. Compound
1-1 Thiophene-2,5-dicarboxylic acid 2-[(2-amino-phenyl)-amide]5-[(1-methyl-butyl)-amide],
1-6 Thiophene-2,5-dicarboxylic acid 2-[(2-amino-phenyl)-amide]5-[(1-methyl-hexyl)-amide],
1-9 Thiophene-2,5-dicarboxylic acid 2-[(2-amino-phenyl)-amide]5-[(3-methoxy-propyl)-amide],
1-10 Thiophene-2,5-dicarboxylic acid 2-[(2-acetylaminoethyl)-amide]5-[(2-amino-phenyl)-amide],
1-11 Thiophene-2,5-dicarboxylic acid 2-[(2-amino-phenyl)-amide]5-[(2-ethyl-hexyl)-amide],
1-13 Thiophene-2,5-dicarboxylic acid 2-[(2-amino-phenyl)-amide]5-[(1,5-dimethyl-hexyl)-amide],
1-15 Thiophene-2,5-dicarboxylic acid 2-[(2-amino-phenyl)-amide]5-[(2-methoxy-1-methyl-ethyl)-amide],
1-20 Thiophene-2,5-dicarboxylic acid 2-[(2-amino-phenyl)-amide]5-pentylamide,
1-21 Thiophene-2,5-dicarboxylic acid 2-[(2-amino-phenyl)-amide]5-butylamide,
1-23 Thiophene-2,5-dicarboxylic acid 2-[ (2-amino-phenyl)-amide]5-[(3-ethoxy-propyl)-amide],
1-24 Thiophene-2,5-dicarboxylic acid 2-[(2-amino-phenyl)-amide]5-sec-butylamide,
1-25 Thiophene-2,5-dicarboxylic acid 2-[(2-amino-phenyl)-amide]5-heptylamide, 1-26 Thiophene-2,5-dicarboxylic acid 2-[(2-amino-phenyl)-amide]5-nonylamide, 1-27 Thiophene-2,5-dicarboxylic acid 2-[(2-amino-phenyl)-amide]5-octylamide, 1-28 Thiophene-2,5-dicarboxylic acid 2-[(2-amino-phenyl)-amide]5-[(1-methyl-heptyl)-amide], 1-29 Thiophene-2,5-dicarboxylic acid 2-[(2-amino-phenyl)-amide]5-(isobutylamide), 1-31 Thiophene-2,5-dicarboxylic acid 2-[(2-amino-phenyl)-amide]5-propylamide, 1-35 Thiophene-2,5-dicarboxylic acid 2-[(2-amino-phenyl)-amide]5-[(2-methyl-butyl)-amide].

Further preferred are compounds of formula I or A or I-A wherein $R^1$ is hydrogen and $R^2$ is $C_{1-12}$-alkyl mono or multiple substituted by —$NR^3R^4$, wherein $R^3$ and $R^4$ independently from each other represent hydrogen or $C_{1-6}$-alkyl.

Examples of such compounds are ex. no. Compound 1-2 Thiophene-2,5-dicarboxylic acid 2-[(2-amino-phenyl)-amide]5-[(4-diethylamino-1-methyl-butyl)-amide], 1-3 Thiophene-2,5-dicarboxylic acid 2-[ (2-amino-phenyl)-amide]5-[(3-diethylamino-propyl)-amide], 1-4 Thiophene-2,5-dicarboxylic acid 2-[(2-amino-phenyl)-amide]5-[(3-dibutylamino-propyl)-amide], 1-5 Thiophene-2,5-dicarboxylic acid 2-[(2-amino-phenyl)-amide]5-[(3-dimethylaminopropyl)-amide], 1-8 Thiophene-2,5-dicarboxylic acid 2-[(2-amino-phenyl)-amide]5-[(3-diisopropylaminoethyl)-amide], 1-17 Thiophene-2,5-dicarboxylic acid 2-[(2-amino-phenyl)-amide]5-[(3-dimethylamino-2,2-dimethylpropyl)-amide], 1-18 Thiophene-2,5-dicarboxylic acid 2-[(2-amino-phenyl)-amide]5-[(2-dimethylaminoethyl)-amide].

Further preferred are compounds of formula I or A or I-A wherein $R^1$ is hydrogen and $R^2$ is alkyl mono or multiple substituted by —$NR^3R^4$, wherein $R^3$ and $R^4$ together with the nitrogen-atom to which they are attached form a ring, which ring is monosubstituted by oxo and which ring may contain a further heteroatom.

An example of such a compound is 1-22 Thiophene-2,5-dicarboxylic acid 2-[(2-amino-phenyl)-amide]5-{[3- (2-oxo-pyrrolidin-1-yl) -propyl]-amide}.

Further preferred are the compounds of formula I or A or I-A, wherein $R^1$ is hydrogen or alkyl and $R^2$ is cycloalkyl or alkyl substituted by cycloalkyl. Such compounds are for example 1-7 Thiophene-2,5-dicarboxylic acid 2-[(2-amino-phenyl)-amide]5-cycloheptylamide, 1-12 Thiophene-2,5-dicarboxylic acid 2-[(2-amino-phenyl)-amide]5-cyclooctylamide, 1-14 Thiophene-2,5-dicarboxylic acid 2-[(2-amino-phenyl)-amide]5-cyclopentylamide, 1-33 Thiophene-2,5-dicarboxylic acid 2-[(2-amino-phenyl)-amide]5-cyclobutylamide, 1-43 Thiophene-2,5-dicarboxylic acid 2-[(2-amino-phenyl)-amide]5-(cyclopropylmethyl-propyl-amide), 1-16 Thiophene-2,5-dicarboxylic acid 2-[(2-amino-phenyl)-amide]5-cyclopropylmethyl-amide.

Further preferred are the compounds of formula I or A wherein Ar is pyridine-2,5-diyl of formula I-B

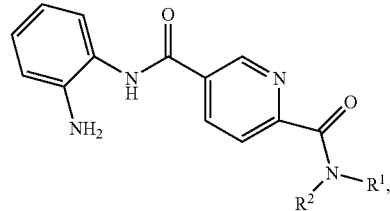

wherein $R^1$ is hydrogen or alkyl; and $R^2$ is hydrogen, $C_{1-}$12-alkyl, $C_{2-12}$-alkenyl, $C_{2-12}$-alkynyl, the alkyl, alkenyl and alkynyl groups being optionally mono or multiple substituted by hydroxy, halogen, alkoxy, alkylsulfanyl, acyloxy, alkoxycarbonyl, acyl, $C_{1-6}$-alkyl-NH—C(O)—, $C_{1-6}$-alkyl-C(O)NH— or —$NR^3R^4$; wherein $R^3R^4$ are as defined above.

Examples of such a compounds are 2-3 Pyridine-2,5-dicarboxylic acid 5-[(2-amino-phenyl)-amide]2-(butyl-methyl-amide), 2-14 Pyridine-2,5-dicarboxylic acid 5-[(2-amino-phenyl)-amide]2-dipropylamide, 2-16 Pyridine-2,5-dicarboxylic acid 5-[(2-amino-phenyl)-amide]2-(methyl-pentyl-amide), 2-17 Pyridine-2,5-dicarboxylic acid 2-(allyl-methyl-amide) 5-[(2-amino-phenyl)-amide], 2-18 Pyridine-2,5-dicarboxylic acid 5-[(2-amino-phenyl)-amide]2-[bis-(2-methoxy-ethyl)-amide], 2-19 Pyridine-2,5-dicarboxylic acid 5-[(2-amino-phenyl)-amide]2-[(2-diethylaminoethyl)-methyl-amide].

Further preferred are the compounds of formula I or A or I-B, wherein $R^1$ is hydrogen and $R^2$ is alkenyl or alkynyl.

An example of such a compound is 2-4 Pyridine-2,5-dicarboxylic acid 2-allylamide 5-[(2-amino-phenyl)-amide].

Further preferred are compounds of formula I or A or I-B, wherein $R^1$ is hydrogen and $R^2$ is unsubstituted straight or branched $C_{1-12}$-alkyl or alkyl mono or multiple substituted by hydroxy, halogen, alkoxy, alkylsulfanyl, acyloxy, alkoxycarbonyl, acyl, $C_{1-6}$-alkyl-NH—C(O)—, or $C_{1-6}$-alkyl-C(O)NH—.

Examples of such compounds are 2-2 Pyridine-2,5-dicarboxylic acid 5-[(2-amino-phenyl)-amide]2-hexylamide, 2-7 Pyridine-2,5-dicarboxylic acid 5-[(2-amino-phenyl)-amide]2-[(2-methoxy-ethyl)-amide], 2-8 Pyridine-2,5-dicarboxylic acid 5-[(2-amino-phenyl)-amide]2-[(3-butoxy-propyl)-amide], 2-9 {[5-(2-amino-phenylcarbamoyl)-pyridine-2-carbonyl]-amino}-acetic acid methyl ester, 2-10 3-{[5-(2-amino-phenylcarbamoyl)-pyridine-2-carbonyl]-amino}-propionic acid tert-butyl ester, 2-11 Pyridine-2,5-dicarboxylic acid 5-[(2-amino-phenyl)-amide]2-[(2,2,3,3,3-pentafluoro-propyl)-amide], 2-12 Pyridine-2,5-dicarboxylic acid 5-[(2-amino-phenyl)-amide]2-[(2,2,3,3,4,4,4-heptafluoro-butyl)-amide], 2-13 Pyridine-2,5-dicarboxylic acid 5-[(2-amino-phenyl)-amide]2-[(1,5-dimethyl-hexyl)-amide], 2-15 Pyridine-2,5-dicarboxylic acid 5-[(2-amino-phenyl)-amide]2-[(1-methyl-hexyl)-amide], 2-20 Pyridine-2,5-dicarboxylic acid 2-[(2-acetylaminoethyl)-amide]5-[(2-amino-phenyl)-amide].

Further preferred are compounds of formula I or A or I-B wherein $R^1$ is hydrogen and $R^2$ is alkyl mono or multiple substituted by —$NR^3R^4$, wherein $R^3$ and $R^4$ independently from each other represent hydrogen or $C_{1-6}$-alkyl.

Examples of such compounds are 2-1 Pyridine-2,5-dicarboxylic acid 5-[(2-amino-phenyl)-amide]2-[(2-diisopropylamino-ethyl)-amide], 2-6 Pyridine-2,5-dicarboxylic acid 5-[(2-amino-phenyl)-amide]2-[(3-dibutylamino-propyl)-amide].

Further preferred are the compounds of formula I or A or I-B, wherein $R^1$ is hydrogen and $R^2$ is cycloalkyl.

An example of such a compound is 2-5 Pyridine-2,5-dicarboxylic acid 5-[(2-amino-phenyl)-amide]2-cyclooctylamide.

Further preferred are compounds of formula I or A wherein Ar signifies pyridine-5,2-diyl of formula I-C

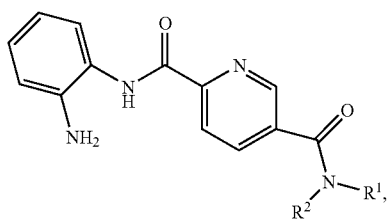

I-C wherein

R1 is hydrogen or alkyl; and $R^2$ is hydrogen, $C_{1-12}$-alkyl, $C_{2-12}$-alkenyl, $C_{2-12}$-alkynyl, the alkyl, alkenyl and alkynyl groups being optionally mono or multiple substituted by hydroxy, halogen, alkoxy, alkylsulfanyl, acyloxy, alkoxycarbonyl, acyl, $C_{1-6}$-alkyl-NH—C(O)—, $C_{1-6}$-alkyl-C(O)NH— or —$NR^3R^4$; wherein $R^3R^4$ are as defined above.

Examples of such compounds are 3-23 pyridine-2,5-dicarboxylic acid 2-[(2-amino-phenyl)-amide]5-(butyl-methyl-amide), 3-24 pyridine-2,5-dicarboxylic acid 5-(allyl-methyl-amide) 2-[(2-amino-phenyl)-amide], 3-25 pyridine-2,5-dicarboxylic acid 2-[(2-amino-phenyl)-amide]5-(methyl-prop-2-ynyl-amide), 3-26 pyridine-2,5-dicarboxylic acid 2-[(2-amino-phenyl)-amide]5-[bis-(2-methoxyethyl)-amide], 3-27 pyridine-2,5-dicarboxylic acid 2-[(2-amino-phenyl)-amide]5-(methyl-pentyl-amide), 3-29 pyridine-2,5-dicarboxylic acid 2-[(2-amino-phenyl)-amide]5-dipropylamide, 3-30 pyridine-2,5-dicarboxylic acid 2-[(2-amino-phenyl)-amide]5-[(2-diethylaminoethyl)-methyl-amide].

Further preferred are the compounds of formula I or A or I-C, wherein $R^1$ is hydrogen and $R^2$ is alkenyl or alkynyl.

An example of such compounds is 3-2 pyridine-2,5-dicarboxylic acid 5-allylamide 2-[(2-amino-phenyl)-amide].

Further preferred are compounds of formula I or A or I-C, wherein $R^1$ is hydrogen and $R^2$ is unsubstituted alkyl or alkyl mono or multiple substituted by hydroxy, halogen, alkoxy, alkylsulfanyl, acyloxy, alkoxycarbonyl, acyl, $C_{1-6}$-alkyl-NH—C(O)—, or $C_{1-6}$-alkyl-C(O)NH—.

Examples of such compounds are 3-3 pyridine-2,5-dicarboxylic acid 2-[(2-amino-phenyl)-amide]5-hexylamide, 3-6 pyridine-2,5-dicarboxylic acid 5-[(2-acetylamino-ethyl)-amide]2-[(2-amino-phenyl)-amide], 3-7 pyridine-2,5-dicarboxylic acid 2-[(2-amino-phenyl)-amide]5-[(2,2,3,3,3-pentafluoro-propyl)-amide], 3-8 pyridine-2,5-dicarboxylic acid 2-[(2-amino-phenyl)-amide]5-[(2,2,3,3,4,4,4-heptafluoro-butyl)-amide], 3-9 3-{[6-(2-amino-phenylcarbamoyl)-pyridine-3-carbonyl]-amino}-butyric acid ethyl ester, 3-10 pyridine-2,5-dicarboxylic acid 2-[(2-amino-phenyl)-amide]5-[(2-hydroxy-propyl)-amide], 3-11 2-{[6-(2-amino-phenylcarbamoyl)-pyridine-3-carbonyl]-amino}-3-methyl-butyric acid methyl ester, 3-12 3-{[6-(2-amino-phenylcarbamoyl)-pyridine-3-carbonyl]-amino}-propionic acid ethyl ester, 3-13 {[6-(2-amino-phenylcarbamoyl)-pyridine-3-carbonyl]-amino}-acetic acid methyl ester, 3-14 pyridine-2,5-dicarboxylic acid 2-[(2-amino-phenyl)-amide]5-[(2-methoxy-ethyl)-amide], 3-15 2-{[6-(2-amino-phenylcarbamoyl)-pyridine-3-carbonyl]-amino}-4-methylsulfanyl-butyric acid methyl ester, 3-16 3-{[6-(2-amino-phenylcarbamoyl)-pyridine-3-carbonyl]-amino}-propionic acid tert-butyl ester, 3-17 pyridine-2,5-dicarboxylic acid 2-[(2-amino-phenyl)-amide]5-[(2,3-dihydroxy-propyl)-amide], 3-18 pyridine-2,5-dicarboxylic acid 2-[(2-amino-phenyl)-amide]5-[(3-butoxy-propyl)-amide], 3-21 pyridine-2,5-dicarboxylic acid 2-[(2-amino-phenyl)-amide]5-sec-butylamide, 3-22 pyridine-2,5-dicarboxylic acid 2-[(2-amino-phenyl)-amide]5-[(1,5-dimethyl-hexyl)-amide], 3-31 pyridine-2,5-dicarboxylic acid 2-[(2-amino-phenyl)-amide]5-[(1-methyl-hexyl)-amide].

Further preferred are compounds of formula I or A or I-C wherein $R^1$ is hydrogen and $R^2$ is alkyl mono or multiple substituted by —$NR^3R^4$, wherein $R^3$ and $R^4$ independently from each other represent hydrogen or $C_{1-6}$-alkyl.

Examples of such compounds are 3-1 pyridine-2,5-dicarboxylic acid 2-[(2-amino-phenyl)-amide]5-[(2-diisopropylamino-ethyl)-amide], 3-5 pyridine-2,5-dicarboxylic acid 2-[(2-amino-phenyl)-amide]5-[(2-dimethylamino-ethyl)-amide], 3-19 pyridine-2,5-dicarboxylic acid 2-[(2-amino-phenyl)-amide]5-[(4-diethylamino-1-methyl-butyl)-amide], 3-20 pyridine-2,5-dicarboxylic acid 2-[(2-amino-phenyl)-amide]5-[(3-dibutylamino-propyl)-amide].

Further preferred are the compounds of formula I or A or I-C, wherein $R^1$ is hydrogen or alkyl and $R^2$ is cycloalkyl.

Example of such compounds are 3-4 pyridine-2,5-dicarboxylic acid 2-[(2-amino-phenyl)-amide]5-cyclooctylamide, 3-28 pyridine-2,5-dicarboxylic acid 2-[(2-amino-phenyl)-amide]5-(cyclopropylmethyl-propyl-amide).

Further preferred are compounds of formula I or A, wherein Ar signifies 1,4-phenylene, namely compounds of formula I-D

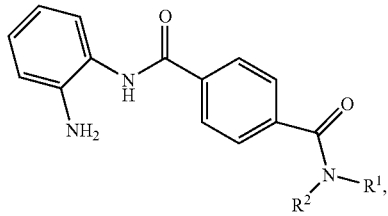

I-D wherein
$R^1$ is hydrogen or alkyl; and
$R^2$ is hydrogen, $C_{1-2}$-alkyl, $C_{2-12}$-alkenyl, $C_{2-12}$-alkynyl, the alkyl, alkenyl and alkynyl groups being optionally mono or multiple substituted by hydroxy, halogen, alkoxy, alkylsulfanyl, acyloxy, alkoxycarbonyl, acyl, $C_{1-6}$-alkyl—NH—C(O)—, $C_{1-6}$-alkyl-C(O)NH— or —$NR^3R^4$; wherein $R^3R^4$ are as defined above.

An example of such a compound is
4-13 N-(2-amino-phenyl)-N'-butyl-N'-methyl-terephthalamide.

Further preferred are the compounds of formula I or A or I-D, wherein $R^1$ is hydrogen and $R^2$ is alkenyl or alkynyl.

Such compounds are for example
4-11 N-allyl-N'-(2-amino-phenyl)-terephthalamide.

Further preferred are compounds of formula I or A or I-D, wherein $R^1$ is hydrogen and $R^2$ is unsubstituted straight or branched alkyl or alkyl mono or multiple substituted by, alkoxy, alkylsulfanyl, acyloxy, alkoxycarbonyl, acyl, $C_{1-6}$-alkyl-NH—C(O)—, or $C_{1-6}$-alkyl-C(O)NH—.

Examples of such compounds are
4-5 N-(2-amino-phenyl)-N'-(2-methoxy-1-methyl-ethyl)-terephthalamide,
4-7 N-(2-amino-phenyl)-N'-(3-ethoxy-propyl)-terephthalamide,
4-12 N-(2-amino-phenyl)-N'-butyl-terephthalamide.

Further preferred are compounds of formula I or A or I-D wherein $R^1$ is hydrogen and $R^2$ is alkyl mono or multiple substituted by —$NR^3R^4$, wherein $R^3$ and $R^4$ independently from each other represent hydrogen or $C_{1-6}$-alkyl.

Examples of such compounds are
4-1 N-(2-amino-phenyl)-N'-(2-diisopropylamino-ethyl)-terephthalamide,
4-2 N-(2-amino-phenyl)-N'-(3-dibutylamino-propyl)-terephthalamide,
4-3 N-(2-amino-phenyl)-N'-(4-diethylamino-1-methyl-butyl)-terephthalamide,
4-4 N-(2-amino-phenyl)-N'-(3-diethylamino-propyl)-terephthalamide,
4-8 N-(2-amino-phenyl)-N'-(2-dimethylamino-ethyl)-terephthalamide,
4-10 N-(2-amino-phenyl)-N'-(3-dimethylamino-2,2-dimethyl-propyl)-terephthalamide.

Further preferred are compounds of formula I or A or I-D, wherein $R^1$ is hydrogen and $R^2$ is alkyl mono or multiple substituted by —$NR^3R^4$, wherein $R^3$ and $R^4$ together with the nitrogen-atom to which they are attached form a ring, which ring is monosubstituted by oxo and which ring may contain a further heteroatom.

An example of such a compound is
4-9 N-(2-amino-phenyl)-N'-[3-(2-oxo-pyrrolidin-1-yl)-propyl]-terephthalamide.

Further preferred are the compounds of formula I or A or I-D, wherein $R^1$ is hydrogen, alkyl or alkenyl and $R^2$ is cycloalkyl or alkyl substituted by cycloalkyl. Such a compound is for example
4-6 N-(2-amino-phenyl)-N'-cyclopropylmethyl-terephthalamide.

Another embodiment of the invention includes compounds of the formula I-E

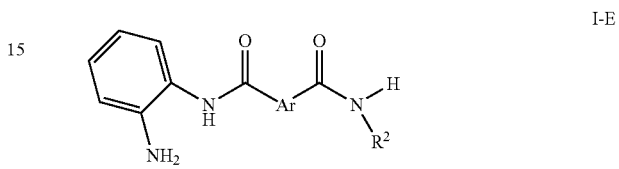

I-E wherein,
Ar is thiophen-2,5-diyl, pyridine-2,5-diyl, pyridine-2,6-diyl, pyridine-2,4-diyl, pyridine-5,2-diyl or 1,4-phenylene; and
$R^2$ represents hydroxyl, alkoxy, $C_2$–$C_{12}$-alkenyloxy or phenoxy, provided that if $R^2$ is hydroxy, Ar is not thiophen-2,5-diyl.

Examples of such compounds are
5-1 Thiophene-2,5-dicarboxylic acid 2-[(2-amino-phenyl)-amide]5-(methoxy-amide),
5-2 Thiophene-2,5-dicarboxylic acid 2-[(2-amino-phenyl)-amide]5-(ethoxy-amide),
5-3 Thiophene-2,5-dicarboxylic acid 2-(allyloxy-amide) 5-[(2-amino-phenyl)-amide],
5-4 Thiophene-2,5-dicarboxylic acid 2-[(2-amino-phenyl)-amide]5-(phenoxy-amide),
5-5 Pyridine-2,5-dicarboxylic acid 2-[(2-amino-phenyl)-amide]5-hydroxyamide,
5-6 Pyridine-2,5-dicarboxylic acid 5-[(2-amino-phenyl)-amide]2-hydroxyamide,
5-7 Pyridine-2,6-dicarboxylic acid 2-[(2-amino-phenyl)-amide]6-hydroxyamide,
5-8 Pyridine-2,4-dicarboxylic acid 2-[(2-amino-phenyl)-amide]4-hydroxyamide.

Still another embodiment of the present invention are the compounds of formula I or A,
Thiophene-2,5-dicarboxylic acid 2-[(2-amino-phenyl)-amide]5-(tert-butoxy-amide),
Pyridine-2,5-dicarboxylic acid 2-(allyl-cyclopentyl-amide) 5-[(2-amino-phenyl)-amide],
Pyridine-2,5-dicarboxylic acid 5-[(2-amino-phenyl)-amide] 2-(cyclopropylmethyl-propyl-amide),
Pyridine-2,5-dicarboxylic acid 5-[(2-amino-phenyl)-amide] 2-sec-butylamide,
Pyridine-2,5-dicarboxylic acid 2-[(2-amino-phenyl)-amide] 5-[(2-hydroxy-ethyl)-amide],
Pyridine-2,5-dicarboxylic acid 2-[(2-amino-phenyl)-amide] 5-{[2-(2-hydroxy-ethoxy)-ethyl]-amide},
Pyridine-2,5-dicarboxylic acid 2-[(2-amino-phenyl)-amide] 5-[(1-cyclohexylmethyl-2-hydroxy-ethyl)-amide],
Pyridine-2,5-dicarboxylic acid 2-[(2-amino-phenyl)-amide] 5-[(4-hydroxy-butyl)-amide],
Pyridine-2,5-dicarboxylic acid 2-[(2-amino-phenyl)-amide] 5-[(1-hydroxymethyl-2-methyl-butyl)-amide],
Pyridine-2,5-dicarboxylic acid 2-[(2-amino-phenyl)-amide] 5-[(4-hydroxy-cyclohexyl)-amide], Pyridine-2,5-dicarboxylic acid 2-[(2-amino-phenyl)-amide] 5-({2-[bis-(2-hydroxy-ethyl)-amino]-ethyl}-amide),
Pyridine-2,5-dicarboxylic acid 5-[(2-amino-phenyl)-amide] 2-[(2-dimethylamino-ethyl)-amide],
Pyridine-2,5-dicarboxylic acid 2-[(2-amino-phenyl)-amide] 5-[(2-dimethylamino-ethyl)-ethyl-amide].

An aromatic dicarboxylic acid derivative of the formula I or A, or a pharmaceutically-acceptable salt thereof, may be prepared by any process known to be applicable to the preparation of chemically-related compounds. Such processes, when used to prepare an aromatic dicarboxylic acid derivative of the formula I or A, or a pharmaceutically-acceptable salt thereof, are provided as a further feature of the invention and are illustrated by the following representative examples in which, unless otherwise stated, Ar, $R^1$ and $R^2$ have the meanings defined above. Starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

EXAMPLES

Example A

One preferred method for the production of compounds of the formula I or A involves the reaction of compounds of the formula II

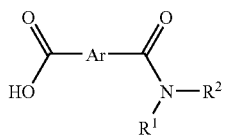

wherein Ar, $R^1$ and $R^2$ are as defined above;
with a compound of the formula III

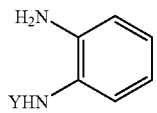

wherein Y represents hydrogen or a suitable amino protecting group.

Protection groups for the amino group are known from peptide chemistry, such protecting groups are for example, benzyloxycarbonyl (cleavage by hydrogenation or hydrobromic acid in acetic acid), t-butoxycarbonyl (cleavage by strong acids, such as, trifluoroacetic acid neat or in dichloromethane, or HCL in dioxane), 9-fluorenmethoxy-carbonyl (cleavage by secondary amines, such as, piperidine).

If $R^2$ in formula A is OH, this hydroxyl group might bear a protecting group for the reaction of $HNR^1R^2$ with compound V or VI as described below. A protection group for the hydroxyl group is, among others, benzyl ether which can be cleaved by hydrogenation. Some of the O-protected $HNR^1R^2$ groups such as O-benzylhydroxylamine are commercially available.

This reaction typically involves a two-step one-pot procedure. In the first step, the carboxylate of the formula II is activated by reaction of the compound in an inert solvent or diluent, for example, in dichloromethane, dioxane, or tetrahydrofuran, in the presence of an activating agent.

A suitable reactive derivative of an acid is, for example, an acyl halide, for example an acyl chloride formed by the reaction of the acid and an inorganic acid chloride, for example thionyl chloride or oxalic acid dichloride; a mixed anhydride, for example an anhydride formed by the reaction of the acid and a chloroformate such as isobutyl chloroformate; an active ester, for example an ester formed by the reaction of the acid and a phenol such as pentafluorophenol; an active ester formed by the reaction of the acid and N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as N-3-dimethylaminopropyl-N-ethylcarbodiimid or dicyclohexyl-carbodiimide; or the product of the reaction of the acid with N,N'-carbonyldiimidazole; or the product of the reaction of the acid and uroniumsalts such as O-(1H-benzotriazol-1-yl)-N,N,N',N',-tetramethyluronium tetrafluoroborate; or the product of the reaction of the acid and phosphorus based reagents, e.g. bis-(2-oxo-3-oxazolidinyl)-phosphorylchloride. The reaction is carried out between −30° C. and 60° C., conveniently at or below 0° C.

In the second step, compound III is added to the solution containing the activated acid. If Y is a protecting group it finally has to be cleaved (methods see above) to yield compound I. In order to obtain the compounds wherein $R^2$ is a hydroxyl group, amino- and hydroxyl protecting groups might both be present in the molecule. In this case the hydroxyl protecting group has to be cleaved before the amino protecting group using the methods described above.

These methods are well known to those skilled in the art. In principle, all methods for the synthesis of amides as used in peptide chemistry as described in e.g. "Methoden der organischen Chemie (Houben-Weyl)" Band XV/1 and XV/2 are also applicable. Monoacylation of unprotected phenylene diamine is described in EP0974576.

Example B

Compounds of formula II can be prepared by hydrolysis from compounds of formula IV

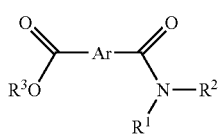

wherein $R^3$ is alkyl or aralkyl, preferably methyl, ethyl, t-butyl, benzyl.

The conditions under which the cleavage is carried out depend on the nature of the group $R^3$. When $R^3$ is an alkyl group such as methyl or ethyl, the reaction is carried out in the presence of a base, for example, lithium hydroxide, sodium hydroxide, or potassium hydroxide in an inert solvent or diluent, for example, in MeOH, ethanol, dioxane, THF, water. When $R^3$ is the t-butyl group, the reaction is carried out in the presence of an acid, for example, a solution of hydrochloric acid in an inert solvent such as diethyl ether or dioxane, or trifluoroacetic acid in dichloromethane. When $R^3$ is the benzyl group, the reaction is carried out by hydrogenolysis in the presence of a noble metal catalyst such as palladium or platinum on a suitable carrier, such as carbon. The methods used for the hydrolysis of the ester are of course dependent on the nature of the residues $R^1$ and $R^2$.

Example C

Compounds of formula IV are prepared from compounds of the formula V wherein Ar and $R^3$ have the meaning defined above.

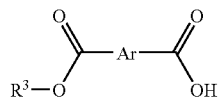
V

This reaction typically involves a two-step one-pot procedure. In the first step, the carboxylate of the formula V is activated using the methods described under Example A.

In the second step, an amine of the formula $HNR^1R^2$ in which $R^1$ and $R^2$ have the meaning defined above is added to the solution, at the temperature used for the activation, and the temperature is slowly adjusted to ambient temperature. An appropriate scavenger base like e.g. triethylamine, or diisopropylethlyamine may be added to the reaction mixture. These methods are well-known to those skilled in the art. In principle, all methods for the synthesis of amides as used in peptide chemistry as described in e.g. "Methoden der organischen Chemie (Houben-Weyl)" Band XV/1 and XV/2 are also applicable.

Example D

There are quite a few compounds of formula V described in the literature. For example, the terephthalic monomethylester is described in e.g. Holba, V., et al., Z. Phys. Chem. 262 (1981) 445–448. It is also commercially available. Pyridine-2,5-dicarboxylic acid 5-methyl ester is described in e.g. WO 93/21146. Thiophene-2,5-dicarboxylic acid monomethyl ester is described in e.g. U.S. Pat. No. 2,680, 731. These monoesters are usually prepared by selective saponification of the diester, but other method may be useful as well and are well known to those skilled in the art.

Example E

Another preferred method for the production of compounds of the formula I or A involves the reaction of compounds of the formula VI

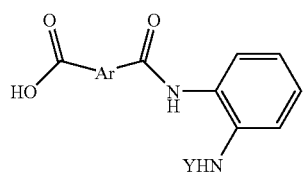
VI wherein Ar has the meaning defined above and Y is suitable protecting group as described in Example A with an amine of the formula $HNR^1R^2$ in which $R^1$ and $R^2$ have the meaning defined hereinbefore.

This reaction typically involves a two-step one-pot procedure and is carried out according to the methods described in Example A.

Finally Y has to be cleaved by methods as described above to give compound I. As mentioned above, if both the amino- and hydroxyl protecting groups are present in the molecule, the hydroxyl protecting group should be cleaved before the amino protecting group.

Example F

Compounds of the formula VI are prepared by hydrolysis as described in Example B from compounds of the formula VII

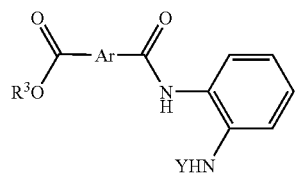
VII wherein $R^3$ and Y have the meaning defined above.

Example G

Compounds of formula VII are prepared from compounds of the formula V wherein A and $R^3$ have the meaning defined hereinbefore

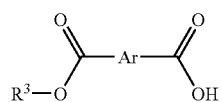
V with a compound of the formula III

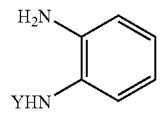
III wherein Y represents a suitable protecting group as described in Example A.

This reaction typically involves a two-step one-pot procedure as described in Example A.

The compounds of formula I or A and their pharmaceutically usable addition salts possess valuable pharmacological properties. It has been found that they possess antiproliferative and differentiation-inducing activity, which results in inhibition of tumor cell proliferation, induction of apoptosis and inhibition of invasion, these compounds are useful for the treatment of diseases such as cancer in humans or animals.

The activity of the compounds according to this invention as HDAC inhibitors is demonstrated using a cellular acetylation assay. In this assay, acetylation of histones is monitored in PC3 cells. High acetylation correlates with inhibition of histone deacetylase by compounds. Cell viability is monitored in parallel to estimate the cytotoxicity of compounds.

PC3 cells, a human prostate carcinoma cell line, are seeded as 1800 cells per well of a 384-well microtiterplate in RPMI 1640 (including 5% FCS, 2 mM glutamine and pen/strep).

After 48 h at 37° C. pre-diluted compounds are added to a final concentration of 1 uM. Compounds are pre-diluted in dimethyl sulfoxide (DMSO) resulting in a final concentration of DMSO of 0.5% per well.

After 24 h incubation cell viability is determined by adding cell proliferation reagent WST-1 (Roche Molecular Biochemicals). Another 60 min later the optical density (OD) is measured (450 nm versus 690 nm).

After measurement the cell layer is prepared for the ELISA reaction. Medium is aspirated and cells are fixed in ethanol at −20° C. for 60 min. After washing with PBS/Tween the blocking solution (PBS/5% FCS/Tween) is added and the cell layer is washed again. Antibodies against acetylated histone H3 or H4 (rabbit polyklonal IgG, Upstate Biotechnologie) are added at a dilution of 1:200 for 60 min at 37° C. As a second antibody goat anti rabbit IgG (H+L) humanIgG adsorbed-HRP conjugate (Dako) is used (1:2000 diluted). Cells are washed 3 times and the peroxidase substrate ABTS is allowed to react for 30–60 min at 37° C. The OD is measured at 405 nm.

The percentage of acetylation is calculated after substraction of blank O.D.s:

$$\frac{\frac{\text{mean O.D. acetylation}}{\text{mean O.D. DMSO control}}}{\frac{\text{mean O.D. DMSO control}}{\text{mean O.D. WST1}}} \times 100\%$$

| Example No. | Compound Name | cell acetylation (PC3, 1 μM) [% of control] |
|---|---|---|
|  | Reference Compound 4-acetylamino-N-(2-aminophenyl)-benzamide | 152 |
| 1-1 | Thiophene-2,5-dicarboxylic acid 2-[(2-aminophenyl)-amide] 5-[(1-methyl-butyl)-amide] | 137.2 |
| 1-4 | Thiophene-2,5-dicarboxylic acid 2-[(2-aminophenyl)-amide] 5-[(3-dibutylamino-propyl)-amide] | 195.7 |
| 1-6 | Thiophene-2,5-dicarboxylic acid 2-[(2-aminophenyl)-amide] 5-[(1-methyl.hexyl)-amide] | 122.9 |
| 1-17 | Thiophene-2,5-dicarboxylic acid 2-[(2-aminophenyl)-amide] 5-[(3-dimethylamino-2,2-dimethylpropyl)-amide] | 149.8 |
| 1-18 | Thiophene-2,5-dicarboxylic acid 2-[(2-aminophenyl)-amide] 5-[(2-dimethylaminoethyl)-amide] | 233.9 |
| 1-19 | Thiophene-2,5-dicarboxylic acid 2-[(2-aminophenyl)-amide] 5-(butyl-methyl-amide) | 118.8 |
| 1-24 | Thiophene-2,5-dicarboxylic acid 2-[(2-aminophenyl)-amide] 5-sec-butylamide | 211.2 |
| 1-35 | Thiophene-2,5-dicarboxylic acid 2-[(2-aminophenyl)-amide] 5-[(2-methyl-butyl)-amide] | 135.4 |
| 1-44 | Thiophene-2,5-dicarboxylic acid 2-amide 5-[(2-amino-phenyl)-amide] | 185.6 |
| 2-1 | Pyridine-2,5-dicarboxylic acid 5-[(2-amino-phenyl)-amide] 2-[(2-diisopropylamino-ethyl)-amide] | 206.6 |
| 3-1 | Pyridine-2,5-dicarboxylic acid 2-[(2-amino-phenyl)-amide] 5-[(2-diisopropylamino-ethyl)-amide] | 244.8 |
| 3-5 | Pyridine-2,5-dicarboxylic acid 2-[(2-amino-phenyl)-amide] 5-[(2-dimethylamino-ethyl)-amide] | 154.6 |
| 3-9 | 3-{[6-(2-amino-phenylcarbamoyl)-pyridine-3-carbonyl]-amino}-butyric acid ethyl ester | 211.6 |
| 3-20 | Pyridine-2,5-dicarboxylic acid 2-[(2-amino-phenyl)-amide] 5-[(3-dibutylamino-propyl)-amide] | 223.8 |
| 4-1 | N-(2-amino-phenyl)-N'-(2-diisopropylamino-ethyl)-terephthalamide | 399.3 |

The new compounds of formula I or A and the pharmaceutically acceptable salts thereof can be used as medicaments, i.e. in form of pharmaceutical preparations. The pharmaceutical preparations can be administered enterally or parenterally in a liquid or solid form. In this connection all the usual forms of administration come into consideration such as for example tablets, capsules, coated tablets, syrups, solutions, suspension, suppositories etc. Water which contains additives such as stabilizers, solubilizers and buffers that are usual in injection solutions is preferably used as the injection medium.

Such additives are e.g. tartrate and citrate buffer, ethanol, complexing agents (such as ethylenediaminetetraacetic acid and non-toxic salts thereof), high-molecular polymers (such as liquid polyethylene glycols) to regulate viscosity. Liquid carrier substances for injection solutions have to be sterile and are preferably dispensed into ampoules. Solid carrier substances are e.g. starch, lactose, mannitol, methylcellulose, talcum, highly dispersed silicic acids, higher molecular fatty acids (such as stearic acid), gelatins, agar-agar, calcium phosphate, magnesium stearate, animal and vegetable fats, solid high-molecular polymers (such as polyethylene glycols); suitable preparations for oral application can optionally also contain flavourings and sweeteners.

Medicaments containing a compound of formula I or A or a pharmaceutically acceptable salt thereof and a therapeutically inert carrier are also an object of the present invention, as is a process for their production, which comprises bringing one or more compounds of formula I or A and/or their pharmaceutically acceptable acid addition salts and, if desired, one or more other therapeutically valuable substances into a galenical administration form together with one or more therapeutically inert carriers.

In accordance with the invention, compounds of formula I or A as well as their pharmaceutically acceptable salts are useful in the control or prevention of illnesses based on their HDAC inhibition and therefore of antiproliferative and differentiation-inducing activity, which results in inhibition of tumor cell proliferation, induction of apoptosis and inhibition of invasion, these compounds are useful for the treatment of diseases such as cancer in humans or animals and for the production of corresponding medicaments.

The dosage depends on various factors such as manner of administration, species, age and/or individual state of health. The doses to be administered daily to a human patient are about 5–400 mg/kg, preferably 10–100 mg/kg and can be taken singly or distributed over several administrations.

The invention will now be illustrated in the following examples in which, unless otherwise stated:
i) evaporations were carried out by rotary evaporation in vacuo and work-up procedures were carried out after removal of residual solids such as drying agents by filtration;
(ii) operations were carried out at ambient temperature, that is in the range 18–25° C. and under an atmosphere of an inert gas such as argon or nitrogen;
(iii) column chromatography (by the flash procedure) and high pressure liquid chromatography (HPLC) were performed on Merck Kieselgel silica or Merck Lichroprep RP-18 reversed-phase silica obtained from E. Merck, Darmstadt, Germany;
(iv) yields are given for illustration only and are not necessarily the maximum attainable;
(v) melting points were determined using a Mettler SP62 automatic melting point apparatus, an oil-bath apparatus or a Kofler hot plate apparatus;
(vi) the structures of the products of the formula I or A were confirmed by nuclear (generally proton) magnetic resonance (NMR) and mass spectral techniques (Micromass Platform II machine using APCI or Micromass Platform ZMD using electrospray);
(vii) intermediates were not generally fully characterized and purity was assessed by thin layer chromatography;
(viii) the following abbreviations have been used:
DMF N,N-dimethylformamide;
DMSO dimethylsulphoxide;
THF tetrahydrofuran;
MeOH methanol;
HCl hydrochloric acid;
NaH sodium hydride
$CH_2Cl_2$ dichloromethane;
$H_2SO_4$ sulphuric acid
sat. saturated
sol. solution
h hour
d days
rt room temperature
eq equivalent Example 1

Preparation of Compounds of Formula I-A

Step 1: 5-(2-tert-Butoxycarbonylamino-phenylcarbamoyl)-thiophene-2-carboxylic acid methyl ester Under an argon atmosphere 21.0 g (129 mmol) carbonyldiimidazol was added to a solution of 24.1 g (129 mmol) thiophene-2,5-dicarboxylic acid monomethyl ester in 600 ml THF. After 2 h at rt 26.9 g (129 mmol) (2-amino-phenyl)-carbamic acid tert-butyl ester were added and the reaction mixture was stirred for further 4 h at rt. The solvent was evaporated and the residue dissolved in 500 ml ethyl acetate. The organic phase was washed three times with 100 ml saturated aqueous $NaHCO_3$ solution, twice with 80 ml water and was dried over sodium sulfate. The solvent was removed down to 80 ml when crystallization started. After 12 h the crystals were filtered off and washed with little ice-cold t-butyl methyl ether and cold heptane. Drying under high vacuum yielded 38.9 g (103.4 mmol) 5-(2-tert-butoxycarbonylamino-phenylcarbamoyl)-thiophene-2-carbox-ylic acid methyl ester, $^1$H-NMR ($D_6$-DMSO) δ=1.45 (s, 9H), 3.87 (s, 3H), 7.14 (m, 1H), 7.22 (m, 1H), 7.46 (m,1H), 7.59 (m, 1H), 7.89 (m, 1H), 7.96 (m, 1H), 8.73 (br, 1H), 10.02 (s, 1H).

Step 2: 5- (2-tert-Butoxycarbonylamino-phenylcarbamoyl)-thiophene-2-carboxylic acid To a suspension of 18.5 g (50 mmol) 5-(2-tert-Butoxycarbonylamino-phenyl-carbamoyl)-thiophene-2-carboxylic acid methyl ester in 500 ml MeOH was added within 20 minutes a solution of 5.6 g (100 mmol) potassium hydroxide in 100 ml water. The reaction mixture was stirred at room temperature for 2 d. The MeOH was evaporated and the remaining aqueous solution was extracted three times with ethylacetate and acidified with a 3 N aqueous HCl solution. The precipitation was filtered off, washed with water and dried at 45° C. in high vacuum to yield 14.5 g (40 mmol) 5-(2-tert-butoxycarbonylamino-phenylcarbamoyl)-thiophene-2-carboxylic acid., $^1$H-NMR ($D_6$-DMSO) δ=1.45 (s, 9H), 7.14 (m, 1H), 7.22 (m, 1H), 7.46 (m, 1H), 7.59 (m, 1H), 7.90 (m, 2H), 8.72 (s, 1H), 9.99 (s, 1H), 13.54 (s, 1H).

Step 3: (2-{[5-(1-Methyl-butylcarbamoyl)-thiophene-2-carbonyl]-amino}-phenyl)-carbamic acid tert-butyl ester To a solution of 4.4 g (12.1 mmol) 5-tert-butoxycarbonylamino-phenylcarbamoyl)-thiophene-2-carboxylic acid in 80 ml THF were added 2.2 g (13.6 mmol) carbonyldiimidazol. The reaction mixture was stirred at 45° C. for 1 h and then cooled to rt. After addition of 1.05 g (12 mmol) 2-pentylamine the reaction mixture was kept at rt for 12 h. The solvent was evaporated and the residue was dissolved in 150 ml $CH_2Cl_2$. The solution was washed twice with 150 ml water each and dried over magnesium sulfate. The solvent was evaporated and the residue was washed with diethyl ether to yield (2-{[5-(1-methyl-butylcarbamoyl)-thiophene-2-carbonyl]-amino}-phenyl)-carbamic acid tert-butyl ester as a white solid, mp. 183° C.

Step 4: Thiophene-2,5-dicarboxylic acid 2-[(2-amino-phenyl)-amide]5-[(1-methyl-butyl)-amide](compound 1-1)

To a solution of 3.3 g (7.65 mmol) (2-{[5-(1-methyl-butylcarbamoyl)-thiophene-2-carbonyl]-amino}-phenyl)-carbamic acid tert-butyl ester in 80 ml MeOH were added 16 ml of a 4M solution of HCl in dioxane under ice cooling. After the solution was stirred for 3 h at rt the solvent was evaporated. To the residue were added 50 ml dichloromethane and 50 ml of a 1M aqueous solution of $NaHCO_3$. After stirring at rt for 30 minutes the precipitation was filtered off, washed with water and dried to yield 2.3 g (6.9 mmol) thiophene-2,5-dicarboxylic acid 2-[(2-amino-phenyl)-amide]5-[(1-methyl-butyl)-amide], mp. 192° C., calculated MW (M+H) 332.14. found (M+H) 332.2. $^1$H-NMR (400 MHz, $(CH_3)_2SO$): δ=9.77 (s, 1H), 8.33 (d, J=8.6 Hz, 1H), 7.92 (m, 1H), 7.78 (m, 1H), 7.13 (m, 1H), 6.99 (m, 1H), 6.78 (m, 1H), 6.59 (m, 1H), 4.96 (s, 2H), 3.97 (m, 1H), 1.57–1.39 (m, 2H), 1.36–1.26 (m, 2H), 1.14 (d, J=6.6 Hz, 3H), 0.88 (t, J=7.1 Hz, 3H).

In analogy to steps 1 to 4 of Example 1 using the appropriate starting material the following compounds where prepared:

| no. | Name | calc. MW (M+H) | found MW (M+H) |
|---|---|---|---|
| 1-2 | thiophene-2,5-dicarboxylic acid 2-[(2-amino-phenyl)-amide] 5-[(4-diethylamino-1-methyl-butyl)-amide]; ¹H-NMR(400MHz, (CH₃)₂SO): δ=9.75(s, 1H), 8.33 (d, J=8.6Hz, 1H), 7.91 (m, 1H), 7.78(m, 1H), 7.13 (m, 1H), 6.98(m, 1H), 6.78 (m, 1H), 6.59(m, 1H), 4.93 (s, 2H), 3.97(m, 1H), 2.46–2.33 (m, 6H), 1.53–1.38 (m, 4H), 1.15(d, J=6.6Hz, 3H), 0.93(t, J=7.1Hz, 6H); | 403.22 | 403.1 |
| 1-3 | thiophene-2,5-dicarboxylic acid 2-[(2-amino-phenyl)-amide] 5-[(3-diethylamino-propyl)-amide]; ¹H-NMR(400MHz, (CD₃)₂SO): δ=9.76(s, 1H), 8.65(t, J=5.05Hz, 1H), 7.92(m, 1H), 7.71(m, 1H), 7.13 (m, 1H), 6.99(m, 1H), 6.78(m, 1H), 6.59(m, 1H), 4.93(s, 2H), 3.27 (m, 2H), 2.46(q, J=7.07Hz, 4H), 2.43(t, J=7.83, 2H), 1.64(m, 2H), 0.95(t, J=7.33, 6H); | 375.19 | 375.1 |
| 1-4 | thiophene-2,5-dicarboxylic acid 2-[(2-amino-phenyl)-amide] 5-[(3-dibutylamino-propyl)-amide]; | 431.25 | 431.1 |
| 1-5 | thiophene-2,5-dicarboxylic acid 2-[(2-amino-phenyl)-amide] 5-[(3-dimethylamino-propyl)-amide]; | 347.15 | 347.3 |
| 1-6 | thiophene-2,5-dicarboxylic acid 2-[(2-amino-phenyl)-amide] 5-[(1-methyl-hexyl)-amide]; ¹H-NMR(400MHz, (CH₃)₂SO): δ=9.75(s, 1H), 8.31 (d, J=8.6Hz, 1H), 7.91(m, 1H), 7.78(m, 1H), 7.14 (m, 1H), 6.98(m, 1H), 6.78(m, 1H), 6.59(m, 1H), 4.93(s, 2H), 3.95 (m, 1H), 1.57–1.41(m, 2H), 1.34–1.22 (m, 6H), 1.14(d, J=6.6Hz, 3H), 0.86(t, J=6.8Hz, 3H); | 360.17 | 360.3 |
| 1-7 | thiophene-2,5-dicarboxylic acid 2-[(2-amino-phenyl)-amide] 5-cycloheptylamide; | 358.16 | 358.2 |
| 1-8 | thiophene-2,5-dicarboxylic acid 2-[(2-amino-phenyl)-amide] 5-[(3-diisopropylamino-ethyl)-amide]; | 389.20 | 389.3 |
| 1-9 | thiophene-2,5-dicarboxylic acid 2-[(2-amino-phenyl)-amide] 5-[(3-methoxy-propyl)-amide]; | 334.12 | 334.2 |
| 1-10 | thiophene-2,5-dicarboxylic acid 2-[(2-acetylamino-ethyl)-amide] 5-[(2-amino-phenyl)-amide]; | 347.12 | 347.2 |
| 1-11 | thiophene-2,5-dicarboxylic acid 2-[(2-amino-phenyl)-amide] 5-[(2-ethyl-hexyl)-amide]; | 374.19 | 374.2 |
| 1-12 | thiophene-2,5-dicarboxylic acid 2-[(2-amino-phenyl)-amide] 5-cyclooctylamide; | 372.17 | 372.2 |
| 1-13 | thiophene-2,5-dicarboxylic acid 2-[(2-amino-phenyl)-amide] 5-[(1,5-dimethyl-hexyl)-amide]; | 374.19 | 374.2 |
| 1-14 | thiophene-2,5-dicarboxylic acid 2-[(2-amino-phenyl)-amide] 5-cyclopentylamide; | 330.13 | 330.2 |
| 1-15 | thiophene-2,5-dicarboxylic acid 2-[(2-amino-phenyl)-amide] 5-[(2-methoxy-1-methyl-ethyl)-amide]; | 334.12 | 334.2 |
| 1-16 | thiophene-2,5-dicarboxylic acid 2-[(2-amino-phenyl)-amide] 5-cyclopropylmethyl-amide; | 316.11 | 316.2 |
| 1-17 | thiophene-2,5-dicarboxylic acid 2-[(2-amino-phenyl)-amide] 5-[(3-dimethylamino-2,2-dimethyl-propyl)-amide]; | 375.19 | 375.2 |
| 1-18 | thiophene-2,5-dicarboxylic acid 2-[(2-amino-phenyl)-amide] 5-[(2-dimethylamino-ethyl)-amide]; ¹H-NMR(400MHz, (CH₃)₂SO): δ= 9.84(s, 1H), 8.84(t, 5.6Hz, 1H), 7.96(m, 1H), 7.74(m, 1H), 7.12 (m, 1H), 6.99(m, 1H), 6.78(m, 1H), 6.59(m, 1H), 4.96(s, 2H), 3.57(m, 2H), 3.19(m, 2H), 2.80(s, 6H); | 333.14 | 333.2 |
| 1-19 | thiophene-2,5-dicarboxylic acid 2-[(2-amino-phenyl)-amide] 5-(butyl-methyl-amide); | 332.14 | 332.3 |
| 1-20 | thiophene-2,5-dicarboxylic acid 2-[(2-amino-phenyl)-amide] 5-pentylamide; | 332.14 | 332.2 |
| 1-21 | thiophene-2,5-dicarboxylic acid 2-[(2-amino-phenyl)-amide] 5-butylamide; | 318.13 | 318.2 |
| 1-22 | thiophene-2,5-dicarboxylic acid 2-[(2-amino-phenyl)-amide] 5-{[3-(2-oxo-pyrrolidin-1-yl)-propyl]-amide}; | 387.15 | 387.1 |
| 1-23 | thiophene-2,5-dicarboxylic acid 2-[(2-amino-phenyl)-amide] 5-[(3-ethoxy-propyl)-amide]; | 348.14 | 348.2 |
| 1-24 | thiophene-2,5-dicarboxylic acid 2-[(2-amino-phenyl)-amide] 5-sec-butylamide; ¹H-NMR(400MHz, (CH₃)₂SO): δ=9.77(s, 1H), 8.32(d, J=8.1Hz, 1H), 7.92 (m, 1H), 7.80(m, 1H), 7.13(m, 1H), 6.98(m, 1H), 6.78(m, 1H), 6.59 (m, 1H), 4.94(s, 2H), 3.87(m, 1H), 1.59–1.44(m, 2H), 1.15(d, J= 6.6Hz, 3H), 0.87(t, J=7.3Hz, 3H); | 318.13 | 318.2 |
| 1-25 | thiophene-2,5-dicarboxylic acid 2-[(2-amino-phenyl)-amide] 5-heptylamide; | 360.17 | 360.2 |
| 1-26 | thiophene-2,5-dicarboxylic acid 2-[(2-amino-phenyl)-amide] 5-nonylamide; | 388.21 | 388.3 |
| 1-27 | thiophene-2,5-dicarboxylic acid 2-[(2-amino-phenyl)-amide] 5-octylamide; | 374.19 | 374.3 |
| 1-28 | thiophene-2,5-dicarboxylic acid 2-[(2-amino-phenyl)-amide] 5-[(1-methyl-heptyl)-amide]; | 374.19 | 374.3 |
| 1-29 | thiophene-2,5-dicarboxylic acid 2-[(2-amino-phenyl)-amide] 5-(isobutyl-amide); | 318.13 | 318.2 |
| 1-30 | thiophene-2,5-dicarboxylic acid 2-[(2-amino-phenyl)-amide] 5-prop-2-ynylamide; | 300.08 | 300.1 |
| 1-31 | thiophene-2,5-dicarboxylic acid 2-[(2-amino-phenyl)-amide] 5-propylamide; | 304.11 | 304.2 |
| 1-32 | thiophene-2,5-dicarboxylic acid 2-allylamide 5-[(2-amino-phenyl)-amide]; | 302.10 | 302.2 |
| 1-33 | thiophene-2,5-dicarboxylic acid 2-[(2-amino-phenyl)-amide] 5-cyclobutylamide; | 316.11 | 316.2 |
| 1-34 | thiophene-2,5-dicarboxylic acid 2-[(2-amino-phenyl)-amide] 5-diethylamide; | 318.13 | 318.2 |

-continued

| no. | Name | calc. MW (M+H) | found MW (M+H) |
|---|---|---|---|
| 1-35 | thiophene-2,5-dicarboxylic acid 2-[(2-amino-phenyl)-amide] 5-[(2-methyl-butyl)-amide]; $^1$H-NMR(400MHz, $(CH_3)_2SO$): δ=9.79(s, 1H), 8.61 (t, 5.8Hz, 1H), 7.93(m, 1H), 7.77(m, 1H), 7.12(m, 1H), 6.99 (m, 1H), 6.78(m, 1H), 6.59 (m, 1H), 4.95(s, 2H), 3.21–3.15 (m, 1H), 3.08–3.02(m, 1H), 1.67–1.57(m, 1H), 1.46–1.36 (m, 1H), 1.17–1.07(m, 1H), 0.89(t, J=7.3Hz, 3H), 0.86(d, J=6.6Hz, 3H); | 332.14 | 332.2 |
| 1-36 | thiophene-2,5-dicarboxylic acid 2-[(2-amino-phenyl)-amide] 5-(methyl-prop-2-ynyl-amide); | 314.10 | 314.1 |
| 1-37 | thiophene-2,5-dicarboxylic acid 2-(allyl-methyl-amide) 5-[(2-amino-phenyl)-amide]; | 316.11 | 316.3 |
| 1-38 | thiophene-2,5-dicarboxylic acid 2-[(2-amino-phenyl)-amide] 5-[(2-dimethylamino-ethyl)-ethyl-amide]; | 361.17 | 361.2 |
| 1-39 | thiophene-2,5-dicarboxylic acid 2-[(2-amino-phenyl)-amide] 5-dipropylamide; | 346.16 | 346.2 |
| 1-40 | thiophene-2,5-dicarboxylic acid 2-[(2-amino-phenyl)-amide] 5-(methyl-pentyl-amide); | 346.16 | 346.2 |
| 1-41 | thiophene-2,5-dicarboxylic acid 2-[(2-amino-phenyl)-amide] 5-[(2-diethylamino-ethyl)-methyl-amide]; | 375.19 | 375.3 |
| 1-42 | thiophene-2,5-dicarboxylic acid 2-[(2-amino-phenyl)-amide] 5-[bis-(2-methoxy-ethyl)-amide]; | 378.15 | 378.1 |
| 1-43 | thiophene-2,5-dicarboxylic acid 2-[(2-amino-phenyl)-amide] 5-(cyclopropylmethyl-propyl-amide); | 358.16 | 358.2 |
| 1-44 | thiophene-2,5-dicarboxylic acid 2-amide 5-[(2-amino-phenyl)-amide]. | 262.07 | 262.2 |

Example 2

Preparation of Compounds of Formula I-B

Step 1: 6-(2-Diisopropylamino-ethylcarbamoyl)-nicotinic acid methyl ester

A suspension of 1.1 g (5 mmol) potassium 5-methoxycarbonyl-pyridine-2-carboxylate, 0.9 ml (12 mmol) thionyl chloride and 0.1 ml DMF in 5 ml dichloroethane was heated at reflux for 2 h. To the reaction mixture 5 ml $CH_2Cl_2$ were added and the solvent was evaporated. This procedure was repeated three times. The residue was suspended in 5 ml $CH_2Cl_2$ and a solution of 9.95 ml (5.5 mmol) 2-diisopropylaminoethylamine, 0.97 ml (7 mmol) triethylamine, 0.1 ml DMF in 5 ml $CH_2Cl_2$ was added under ice-cooling. After stirring for 12 h at rt the organic phase was extracted with water, 5% citric acid and aqueous $NaHCO_3$ and dried over magnesium sulfate. After evaporation of the solvent the residue was subjected to silica gel chromatography (20% MeOH and 1% triethylamine in ethyl acetate) to yield 1.15 g (3.7 mmol) 6-(2-diisopropylamino-ethylcarbamoyl)-nicotinic acid methyl ester; exact MW [M+H] calcd: 308.20; MW .found [M+H]: 308.20.

Step 2: 6-(2-Diisopropylamino-ethylcarbamoyl)-nicotinic acid

To a solution of 1100 mg (3.6 mmol) 6-(2-diisopropylamino-ethylcarbamoyl)-nicotinic acid methyl ester in 10 ml THF and 3.0 ml MeOH was added 3.6 ml of an 2N aqueous NaOH solution. After 4 h at rt the solvent was evaporated. The residue was acidified with 1N HCl, filtered off and washed with water to give 936 mg (3.2 mmol) 6-(2-diisopropylamino-ethylcarbamoyl)-nicotinic acid; exact MW [M+H] calc'd: 294.18; MW .found [M+H]: 209.15.

Step 3: Pyridine-2,5-dicarboxylic acid 5-[(2-amino-phenyl)-amide]2-[(2-diisopropylamino-ethyl)-amide] compound (2-1)

A solution of 936 mg (3.2 mmol) 6-(2-diisopropylamino-ethylcarbamoyl)-nicotinic acid and 518 mg (3.2 mmol) carbonyldiimidazol in 8 ml THF was heated at 45° C. for 1 h and then cooled to rt. 1.38 g (12.8 mmol) phenylenediamine and 0.5 ml (6.4 mmol) trifluoroacetic acid were added and stirred for 20 h at rt. The solvent was evaporated and aqueous ammonia solution was added to the residue. The aqueous phase was extracted with $CH_2Cl_2$ and the solvent was evaporated from the combined organic phases. The residue was subjected silica gel chromatography (ethyl acetate then 20% MeOH and 1% triethylamine in ethyl acetate) to yield 404 mg (1.06 mmol) pyridine-2,5-dicarboxylic acid 5-[(2-amino-phenyl)-amide]2-[(2-diisopropylamino-ethyl)-amide]; exact MW [M+H] calc'd: 384.24; MW found [M+H]: 384.23.

The compounds listed below have been prepared according to the method described in example 2 steps 1 to 3

| no. | Name | calc. MW (M+H) | found MW (M+H) |
|---|---|---|---|
| 2-1 | pyridine-2,5-dicarboxylic acid 5-[(2-amino-phenyl)-amide] 2-[(2-diisopropylamino-ethyl)-amide]; $^1$H-NMR(400MHz, $(CH_3)_2SO$): δ=9.93(s, 1H), 9.16(m, 1H), 8.84(t, J=5.8Hz, 1H), 8.50(m, 1H), 8.15(m, 1H), 7.17(m, 1H), 6.99(m, 1H), 6.78(m, 1H), 6.59(m, 1H), 5.2 (s, 2H), 3.29(m, 2H), 3.00(m, 2H), 2.58(t, J=7.3Hz, 2H), 0.99 (d, J=6.6Hz, 12H); | 384.24 | 384.2 |
| 2-2 | pyridine-2,5-dicarboxylic acid 5-[(2-amino-phenyl)-amide] 2-hexylamide; | 341.20 | 341.2 |
| 2-3 | pyridine-2,5-dicarboxylic acid 5-[(2-amino-phenyl)-amide] 2-(butyl-methyl-amide); | 327.18 | 327.2 |
| 2-4 | pyridine-2,5-dicarboxylic acid 2-allylamide 5-[(2-amino-phenyl)-amide]; | 297.14 | 297.2 |
| 2-5 | pyridine-2,5-dicarboxylic acid 5-[(2-amino-phenyl)-amide] 2-cyclooctylamide; | 367.21 | 367.2 |
| 2-6 | pyridine-2,5-dicarboxylic acid 5-[(2-amino-phenyl)-amide] 2-[(3-dibutylamino-propyl)-amide]; | 426.29 | 426.3 |
| 2-7 | pyridine-2,5-dicarboxylic acid 5-[(2-amino-phenyl)-amide] 2-[(2-methoxy-ethyl)-amide]; | 315.15 | 315.1 |
| 2-8 | pyridine-2,5-dicarboxylic acid 5-[(2-amino-phenyl)-amide] 2-[(3-butoxy-propyl)-amide]; | 371.21 | 371.3 |

-continued

| no. | Name | calc. MW (M+H) | found MW (M+H) |
|---|---|---|---|
| 2-9 | {[5-(2-amino-phenylcarbamoyl)-pyridine-2-carbonyl]-amino}-acetic acid methyl ester; | 329.12 | 329.1 |
| 2-10 | 3-{[5-(2-amino-phenylcarbamoyl)-pyridine-2-carbonyl]-amino}-propionic acid tert-butyl ester; | 385.19 | 385.3 |
| 2-11 | pyridine-2,5-dicarboxylic acid 5-[(2-amino-phenyl)-amide] 2-[(2,2,3,3,3-pentafluoro-propyl)-amide]; | 389.10 | 389.1 |
| 2-12 | pyridine-2,5-dicarboxylic acid 5-[(2-amino-phenyl)-amide] 2-[(2,2,3,3,4,4,4-heptafluoro-butyl)-amide]; | 439.10 | 439.1 |
| 2-13 | pyridine-2,5-dicarboxylic acid 5-[(2-amino-phenyl)-amide] 2-[(1,5-dimethyl-hexyl)-amide]; | 369.23 | 369.3 |
| 2-14 | pyridine-2,5-dicarboxylic acid 5-[(2-amino-phenyl)-amide] 2-dipropylamide; | 341.20 | 341.3 |
| 2-15 | pyridine-2,5-dicarboxylic acid 5-[(2-amino-phenyl)-amide] 2-[(1-methyl-hexyl)-amide]; | 355.21 | 355.4 |
| 2-16 | pyridine-2,5-dicarboxylic acid 5-[(2-amino-phenyl)-amide] 2-(methyl-pentyl-amide); | 341.20 | 341.2 |
| 2-17 | pyridine-2,5-dicarboxylic acid 2-(allyl-methyl-amide) 5-[(2-amino-phenyl)-amide]; | 311.15 | 311.3 |
| 2-18 | pyridine-2,5-dicarboxylic acid 5-[(2-amino-phenyl)-amide] 2-[bis-(2-methoxy-ethyl)-amide]; | 373.19 | 373.3 |
| 2-19 | pyridine-2,5-dicarboxylic acid 5-[(2-amino-phenyl)-amide] 2-[(2-diethylamino-ethyl)-methyl-amide]; | 370.22 | 370.4 |
| 2-20 | pyridine-2,5-dicarboxylic acid 2-[(2-acetylamino-ethyl)-amide] 5-[(2-amino-phenyl)-amide]; | 342.16 | 342.1 |
| 2-21 | pyridine-2,5-dicarboxylic acid 2-(allyl-cyclopentyl-amide) 5-[(2-amino-phenyl)-amide]; | 365.45 | 365.3 |
| 2-22 | pyridine-2,5-dicarboxylic acid 5-[(2-amino-phenyl)-amide] 2-(cyclopropylmethyl-propyl-amide); | 353.44 | 353.3 |
| 2-23 | pyridine-2,5-dicarboxylic acid 5-[(2-amino-phenyl)-amide] 2-sec-butylamide; | 313.38 | 313.23 |
| 2-24 | pyridine-2,5-dicarboxylic acid 5-[(2-amino-phenyl)-amide] 2-[(2-dimethylamino-ethyl)-amide]. | 328.39 | 328.16 |

Example 3

Preparation of Compounds of Formula I-C

In an analogous manner to that described in the example 1, and using known methods as described in the literature (e.g. in standard works such as Houben-Weyl, "Methoden der Organischen Chemie, Georg Thieme Verlag"; Stuttgart; Organic Reactions, John Wiley & Sons, Inc., New York) the following compounds are prepared:

| no. | Name | calc. MW (M+H) | found MW (M+H) |
|---|---|---|---|
| 3-1 | pyridine-2,5-dicarboxylic acid 2-[(2-amino-phenyl-amide] 5-[(2-diisopropylamino-ethyl)-amide]; $^1$H-NMR(400MHz, (CD$_3$)$_2$SO): δ=10.1(s, 1H), 9.09(m, 1H), 8.77(t, J=5.3Hz, 1H), 8.41 (m, 1H), 8.22(m, 1H), 7.47(m, 1H), 6.97(m, 1H), 6.83(m, 1H), 6.65(m, 1H), 4.92(s, 2H), 3.27–3.23(m, 2H), 2.99 (m, 2H), 2.56(t, J=7.3Hz, 2H), 0.99(d, J=6.6Hz, 12H); | 384.24 | 384.2 |
| 3-2 | pyridine-2,5-dicarboxylic acid 5-allylamide 2-[(2-amino-phenyl)-amide]; | 297.14 | 297.2 |
| 3-3 | pyridine-2,5-dicarboxylic acid 2-[(2-amino-phenyl)-amide] 5-hexylamide; | 341.20 | 341.3 |
| 3-4 | pyridine-2,5-dicarboxylic acid 2-[(2-amino-phenyl)-amide] 5-cyclooctylamide; | 367.21 | 367.3 |
| 3-5 | pyridine-2,5-dicarboxylic acid 2-[(2-amino-phenyl)-amide] 5-[(2-dimethylamino-ethyl)-amide]; $^1$H-NMR(400MHz, (CH$_3$)$_2$SO): δ=10.11(s, 1H), 9.09(m, 1H), 8.77(t, J=5.3 Hz, 1H), 8.41(m, 1H), 8.22(m, 1H), 7.48(m, 1H), 6.97(m, 1H), 6.83(m, 1H), 6.66(m, 1H), 4.91(s, 2H), 3.41(m, 2H), 2.44(t, J=6.8 Hz, 2H), 2.20(s, 6H); | 328.18 | 328.2 |
| 3-6 | pyridine-2,5-dicarboxylic acid 5-(2-acetylamino-ethyl)-amide] 2-[(2-amino-phenyl)-amide]; | 342.16 | 342.2 |
| 3-7 | pyridine-2,5-dicarboxylic acid 2-[(2-amino-phenyl)-amide] 5-[(2,2,3,3,3-pentafluoro-propyl)-amide]; | 389.10 | 389.1 |
| 3-8 | pyridine-2,5-dicarboxylic acid 2-[(2-amino-phenyl)-amide] 5-[(2,2,3,3,4,4,4-heptafluoro-butyl)-amide]; | 439.10 | 439.1 |
| 3-9 | 3-{[6-(2-amino-phenylcarbamoyl)-pyridine-3-carbonyl]-amino}-butyric acid ethyl ester; | 371.17 | 371.2 |
| 3-10 | pyridine-2,5-dicarboxylic acid 2-[(2-amino-phenyl)-amide] 5-[(2-hydroxy-propyl)-amide]; | 315.15 | 315.2 |
| 3-11 | 2-{[6-(2-amino-phenylcarbamoyl)-pyridine-3-carbonyl]-amino}-3-methyl-butyric acid methyl ester; | 371.17 | 371.2 |
| 3-12 | 3-{[6-(2-amino-phenylcarbamoyl)-pyridine-3-carbonyl]-amino}-propionic acid ethyl ester; | 357.16 | 357.1 |
| 3-13 | {[6-(2-amino-phenylcarbamoyl)-pyridine-3-carbonyl]-amino}-acetic acid methyl ester; | 329.12 | 329.1 |
| 3-14 | pyridine-2,5-dicarboxylic acid 2-[(2-amino-phenyl)-amide] 5-[(2-methoxy-ethyl)-amide]; | 315.15 | 315.1 |
| 3-15 | 2-{[6-(2-amino-phenylcarbamoyl)-pyridine-3-carbonyl]-amino}-4-methylsulfanyl-butyric acid methyl ester; | 403.14 | 403.1 |

| no. | Name | calc. MW (M+H) | found MW (M+H) |
|---|---|---|---|
| 3-16 | 3-{[6-(2-amino-phenylcarbamoyl)-pyridine-3-carbonyl]-amino}-propionic acid tert-butyl ester; | 385.19 | 385.3 |
| 3-17 | pyridine-2,5-dicarboxylic acid 2-[(2-amino-phenyl)-amide] 5-[(2,3-dihydroxy-propyl)-amide]; | 331.14 | 331.2 |
| 3-18 | pyridine-2,5-dicarboxylic acid 2-[(2-amino-phenyl)-amide] 5-[(3-butoxy-propyl)-amide]; | 371.21 | 371.3 |
| 3-19 | pyridine-2,5-dicarboxylic acid 2-[(2-amino-phenyl)-amide] 5-[(4-diethylamino-1-methyl-butyl)-amide]; | 398.26 | 398.3 |
| 3-20 | pyridine-2,5-dicarboxylic acid 2-[(2-amino-phenyl)-amide] 5-[(3-dibutylamino-propyl)-amide]; | 426.29 | 426.3 |
| 3-21 | pyridine-2,5-dicarboxylic acid 2-[(2-amino-phenyl)-amide] 5-sec-butylamide; | 313.17 | 313.2 |
| 3-22 | pyridine-2,5-dicarboxylic acid 2-[(2-amino-phenyl)-amide] 5-[(1,5-dimethyl-hexyl)-amide]; | 369.23 | 369.3 |
| 3-23 | pyridine-2,5-dicarboxylic acid 2-[(2-amino-phenyl)-amide] 5-(butyl-methyl-amide); | 327.18 | 327.3 |
| 3-24 | pyridine-2,5-dicarboxylic acid 5-(allyl-methyl-amide) 2-[(2-amino-phenyl)-amide]; | 311.15 | 311.3 |
| 3-25 | pyridine-2,5-dicarboxylic acid 2-[(2-amino-phenyl)-amide] 5-(methyl-prop-2-ynyl-amide); | 309.14 | 309.1 |
| 3-26 | pyridine-2,5-dicarboxylic acid 2-[(2-amino-phenyl)-amide] 5-[bis-(2-methoxy-ethyl)-amide]; | 373.19 | 373.2 |
| 3-27 | pyridine-2,5-dicarboxylic acid 2-[(2-amino-phenyl)-amide] 5-(methyl-pentyl-amide); | 341.20 | 341.2 |
| 3-28 | pyridine-2,5-dicarboxylic acid 2-[(2-amino-phenyl)-amide] 5-(cyclopropylmethyl-propyl-amide); | 353.20 | 353.2 |
| 3-29 | pyridine-2,5-dicarboxylic acid 2-[(2-amino-phenyl)-amide] 5-dipropylamide; | 341.20 | 341.3 |
| 3-30 | pyridine-2,5-dicarboxylic acid 2-[(2-amino-phenyl)-amide] 5-[(2-diethylamino-ethyl)-methyl-amide]; | 370.22 | 370.4 |
| 3-31 | pyridine-2,5-dicarboxylic acid 2-[(2-amino-phenyl)-amide] 5-[(1-methyl-hexyl)-amide]; | 355.21 | 355.3 |
| 3-32 | pyridine-2,5-dicarboxylic acid 2-[(2-amino-phenyl)-amide] 5-[(2-hydroxy-ethyl)-amide]; | 301.32 | 301.13 |
| 3-33 | pyridine-2,5-dicarboxylic acid 2-[(2-amino-phenyl)-amide] 5-{[2-(2-hydroxy-ethoxy)-ethyl]-amide}; | 345.38 | 345.13 |
| 3-34 | pyridine-2,5-dicarboxylic acid 2-[(2-amino-phenyl)-amide] 5-[(1-cyclohexylmethyl-2-hydroxy-ethyl)-amide]; | 397.5 | 397.15 |
| 3-35 | pyridine-2,5-dicarboxylic acid 2-[(2-amino-phenyl)-amide] 5-[(4-hydroxy-butyl)-amide]; | 329.38 | 329.11 |
| 3-36 | pyridine-2,5-dicarboxylic acid 2-[(2-amino-phenyl)-amide] 5-[(1-hydroxymethyl-2-methyl-butyl)-amide]; | 357.43 | 357.15 |
| 3-37 | pyridine-2,5-dicarboxylic acid 2-[(2-amino-phenyl)-amide] 5-[(4-hydroxy-cyclohexyl)-amide]; | 355.42 | 355.13 |
| 3-38 | pyridine-2,5-dicarboxylic acid 2-[(2-amino-phenyl)-amide] 5-({2-[bis-(2-hydroxy-ethyl)-amino]-ethyl}-amide); | 388.45 | 388.2 |
| 3-39 | pyridine-2,5-dicarboxylic acid 2-[(2-amino-phenyl)-amide] 5-[(2-dimethylamino-ethyl)-ethyl-amide]. | 356.45 | 356.3 |

Example 4

Preparation of Compounds of Formula I-D

The terephthalamide derivatives of formula I-D were prepared in an analogous manner to that described in the example 1,

| no. | Name | calc. MW (M+H) | found MW (M+H) |
|---|---|---|---|
| 4-1 | N-(2-amino-phenyl)-N'-(2-diisopropylamino-ethyl)-terephthalamide; $^1$H-NMR(400MHz, (CH$_3$)$_2$SO): δ=9.77(s, 1H), 8.54(t, J=5.3Hz, 1H), 8.06(m, 2H), 7.95(m, 2H), 7.18(m, 1H), 6.99(m, 1H), 6.79(m, 1H), 6.60(m, 1H), 4.94(s, 2H), 3.23(m, 2H), 2.98(m, 2H), 2.54(t, J=7.3Hz, 2H), 0.99(d, J=6.6Hz, 12H); | 383.24 | 383.3 |
| 4-2 | N-(2-amino-phenyl)-N'-(3-dibutylamino-propyl)-terephthalamide; | 425.29 | 425.3 |
| 4-3 | N-(2-amino-phenyl)-N'-(4-diethylamino-1-methyl-butyl)-terephthalamide; | 397.26 | 397.2 |
| 4-4 | N-(2-amino-phenyl)-N'-(3-diethylamino-propyl)-terephthalamide; | 369.23 | 369.3 |
| 4-5 | N-(2-amino-phenyl)-N'-(2-methoxy-1-methyl-ethyl)-terephthalamide; | 328.17 | 328.2 |
| 4-6 | N-(2-amino-phenyl)-N'-cyclopropylmethyl-terephthalamide; | 310.16 | 310.2 |
| 4-7 | N-(2-amino-phenyl)-N'-(3-ethoxy-propyl)-terephthalamide; | 342.18 | 342.3 |
| 4-8 | N-(2-amino-phenyl)-N'-(2-dimethylamino-ethyl)-terephthalamide; | 327.18 | 327.3 |
| 4-9 | N-(2-amino-phenyl)-N'-[3-(2-oxo-pyrrolidin-1-yl)-propyl]-terephthalamide; | 381.19 | 381.3 |
| 4-10 | N-(2-amino-phenyl)-N'-(3-dimethylamino-2,2-dimethyl-propyl)-terephthalamide; | 369.23 | 369.3 |
| 4-11 | N-allyl-N'-(2-amino-phenyl)-terephthalamide; | 296.14 | 296.2 |
| 4-12 | N-(2-amino-phenyl)-N'-butyl-terephthalamide; | 312.17 | 312.2 |
| 4-13 | N-(2-amino-phenyl)-N'-butyl-N'-methyl-terephthalamide. | 326.19 | 326.3 |

Example 5

Preparation of Compounds of Formula I-E

In analogy to steps 1 to 4 of Example 1 and using the corresponding starting materials the following compounds were prepared:

| no. | Name | calc. MW (M+H) | found MW (M+H) |
|---|---|---|---|
| 5-1 | thiophene-2,5-dicarboxylic acid 2-[(2-amino-phenyl)-amide] 5-(methoxy-amide), | 292.08 | 292.2 |
| 5-2 | thiophene-2,5-dicarboxylic acid 2-[(2-amino-phenyl)-amide] 5-(ethoxy-amide), | 306.09 | 306.1 |
| 5-3 | thiophene-2,5-dicarboxylic acid 2-(allyloxy-amide) 5-[(2-amino-phenyl)-amide], H-NMR(400MHz, $(CH_3)_2SO$): δ=11.90 (s, 1H), 9.82(s, 1H), 7.93 (m, 1H), 7.78(m, 1H), 7.65 (m, 1H), 7.12(m, 1H), 6.99 (m, 1H), 6.78(m, 1H), 6.59 (m, 1H), 6.05–5.95(m, 1H), 5.39–5.35(m, 1H), 5.30–5.28 (m, 1H), 4.95(s, 2H), 4.42 (d, J=6.1Hz, 1H), | 318.09 | 318.2 |
| 5-4 | thiophene-2,5-dicarboxylic acid 2-[(2-amino-phenyl)-amide] 5-(phenoxy-amide), | 354.09 | 354.2 |
| 5-5 | pyridine-2,5-dicarboxylic acid 2-[(2-amino-phenyl)-amide] 5-hydroxyamide, H-NMR (400MHz, $(CH_3)_2SO$): δ= 11.61(s, 1H), 10.12(s, 1H), 9.36(s, 1H), 9.02(m, 1H), 8.35 (m, 1H), 8.21(m, 1H), 7.47 (m, 1H), 6.97(m, 1H), 6.83 (m, 1H), 6.66(m, 1H), 4.94 (s, 2H), | 273.10 | 273.2 |
| 5-6 | pyridine-2,5-dicarboxylic acid 5-[(2-amino-phenyl)-amide] 2-hydroxyamide, | 273.10 | 273.1 |
| 5-7 | pyridine-2,6-dicarboxylic acid 2-[(2-amino-phenyl)-amide] 6-hydroxyamide, | 273.10 | 273.1 |
| 5-8 | pyridine-2,4-dicarboxylic acid 2-[(2-amino-phenyl)-amide] 4-hydroxyamide, | 273.10 | 273.1 |
| 5-9 | thiophene-2,5-dicarboxylic acid 2-[(2-amino-phenyl)-amide] 5-(tert-butoxy-amide). | 334.41 | 334.2 |

Example 6

Tablet Formulation (Wet Granulation):

| Item | Ingredients | mg/tablet | | | |
|---|---|---|---|---|---|
| 1. | Compound of formula I or A | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula I or A | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

The effect of the compounds according to the invention may further be assessed by the following test:

Method

Male NMRI nu/nu-mice(n=15 per group), aged 8–10 weeks, are subcutaneously injected with $5*10^6$ PC-3 prostate carcinoma cells. On day 10, animals with tumor volumes of about 150 mm³ are randomly assigned to treatment groups. The test compound is administered as a microsuspension in 7.5% Gelatine—0.22% NaCl— Suspension with an application volume of 10 ml/kg based on actual body weights. Once daily oral treatment is performed from approximately day 10 to day 27 on a 5–7 times per week treatment schedule.

The volume of the tumor is determined from the following equation:

$$\text{Volume of a tumor} = \tfrac{1}{2}ab^2,$$

where "a" and "b" are the long and the short diameters of the tumor, respectively. At the conclusion of treatment, measurement of the volume of the tumor is taken and compared to the original tumor volume to determine tumor volume reduction.

What is claimed is:
1. A compound of formula A

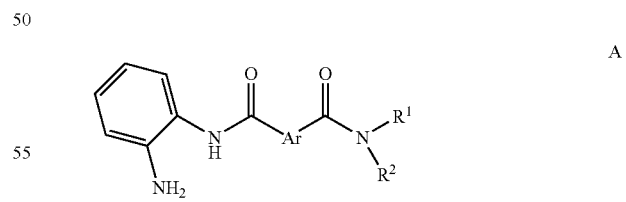

wherein

Ar is pyridine-2,5-diyl, pyridine-5,2-diyl, pyridine-2,6-diyl, or pyridine-2,4-diyl, $R^1$, $R^2$ are each independently selected from hydrogen, substituted or unsubstituted $C_{1-12}$-alkyl, substituted or unsubstituted $C_{2-12}$-alkenyl, substituted or unsubstituted $C_{2-12}$-alkynyl, and substituted or unsubstituted $C_{3-12}$-cycloalkyl, wherein the substituent is selected from hydroxy, halogen, $C_{3-12}$-cycloalkyl, alkoxy, alkylsulfanyl, acyloxy, alkoxycarbonyl, acyl, $C_{1-6}$-alkyl-NH—C(O)—, $C_{1-6}$-alkyl-C(O)NH— and —NR$^3$R$^4$, or alternatively R$^1$ is hydrogen, and R$^2$ is hydroxy, alkoxy, $C_2$–$C_{12}$-alkenyloxy, phenoxy, or phenoxy substituted with methyl, methoxy, halogen, nitro, cyano, trifluoromethyl, ethenyl or —C(O)—O—CH$_3$; and R$^3$ and R$^4$ are each independently selected from hydrogen or $C_{1-6}$-alkyl, or alternatively R$^3$ and R$^4$ together with the nitrogen-atom to which they are attached form a ring, which ring is monosubstituted by oxo and which ring optionally contains a further heteroatom, or a pharmaceutically acceptable salt thereof.

2. The compound according to claim 1 wherein,

Ar is pyridine-2,5-diyl or pyridine-5,2-diyl,

R$^1$, R$^2$ are each independently selected from hydrogen, substituted or unsubstituted $C_{1-12}$-alkyl, substituted or unsubstituted $C_{2-12}$-alkenyl, substituted or unsubstituted $C_{2-12}$-alkynyl, and substituted or unsubstituted $C_{3-12}$-cycloalkyl, where the substituent is selected from hydroxy, halogen, $C_{3-12}$-cycloalkyl, alkoxy, alkylsulfanyl, acyloxy, alkoxycarbonyl, acyl, $C_{1-6}$-alkyl-NH—C(O)—, $C_{1-6}$-alkyl-C(O)NH— and —NR$^3$R$^4$, R$^3$ and R$^4$ are each independently selected from hydrogen or $C_{1-6}$-alkyl, or alternatively R$^3$ and R$^4$ together with the nitrogen-atom to which they are attached form a ring, which ring is monosubstituted by oxo and which ring optionally contains a further heteroatom.

3. The compound according to claim 2, wherein:

R$^1$ is hydrogen or alkyl, and

R$^2$ is hydrogen, substituted or unsubstituted $C_{1-12}$-alkyl, substituted or unsubstituted $C_{2-12}$-alkenyl, or substituted or unsubstituted $C_{2-12}$-alkynyl, wherein the substituent is selected from hydroxy, halogen, alkoxy, alkylsulfanyl, acyloxy, alkoxycarbonyl, acyl, $C_{1-6}$-alkyl-NH—C(O)—, $C_{1-6}$-alkyl-C(O)NH— and —NR$^3$R$^4$.

4. The compound according to claim 2, wherein:

R$^1$ is hydrogen, and

R$^2$ is alkenyl or alkynyl.

5. The compound according to claim 2, wherein:

R$^1$ is hydrogen, and

R$^2$ is unsubstituted straight or branched $C_{1-12}$-alkyl or alkyl substituted by alkoxy, alkylsulfanyl, acyloxy, alkoxycarbonyl, acyl, $C_{1-6}$-alkyl-NH—C(O)—, or $C_{1-6}$-alkyl-C(O)NH—.

6. The compound according to claim 2, wherein:

R$^1$ is hydrogen, and

R$^2$ is $C_{1-12}$-alkyl substituted by at least one —NR$^3$R$^4$, wherein R$^3$ and R$^4$ are each independently selected from hydrogen and $C_{1-6}$-alkyl.

7. The compound according to claim 2, wherein:

R$^1$ is hydrogen, and

R$^2$ is alkyl substituted by at least one —NR$^3$R$^4$, wherein R$^3$ and R$^4$ together with the nitrogen-atom to which they are attached form a ring, which ring is monosubstituted by oxo and which ring optionally contains at least one heteroatom.

8. The compound according to claim 2, wherein:

R$^1$ is hydrogen or alkyl, and

R$^2$ is cycloalkyl or alkyl substituted by cycloalkyl.

9. The compound according to claim 2, wherein Ar is pyridine-2,5-diyl, the compound having formula I-B

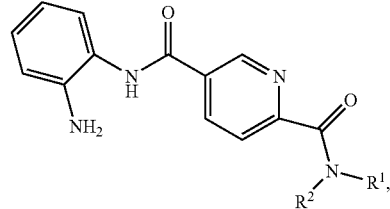

I-B wherein

R$^1$ is hydrogen or alkyl; and

R$^2$ is hydrogen, substituted or unsubstituted $C_{1-12}$-alkyl, substituted or unsubstituted $C_{2-12}$-alkenyl, or substituted or unsubstituted $C_{2-12}$-alkynyl, wherein the substituent is selected from hydroxy, halogen, alkoxy, alkylsulfanyl, acyloxy, alkoxycarbonyl, acyl, $C_{1-6}$-alkyl-NH—C(O)—, $C_{1-6}$-alkyl-C(O)NH— and —NR$^3$R$^4$.

10. The compound according to claim 9, wherein the compound is selected from pyridine-2,5-dicarboxylic acid 5-[(2-amino-phenyl)-amide]2-(butyl-methyl-amide), pyridine-2,5-dicarboxylic acid 5-[(2-amino-phenyl)-amide]2-dipropylamide, pyridine-2,5-dicarboxylic acid 5-[(2-amino-phenyl)-amide]2-(methyl-pentyl-amide), pyridine-2,5-dicarboxylic acid 2-(allyl-methyl-amide) 5-[(2-amino-phenyl)-amide], pyridine-2,5-dicarboxylic acid 5-[(2-amino-phenyl)-amide]2-[bis-(2-methoxy-ethyl)-amide], and pyridine-2,5-dicarboxylic acid 5-[(2-amino-phenyl)-amide]2-[(2-diethylaminoethyl)-methyl-amide].

11. The compound according to claim 9, wherein:

R$^1$ is hydrogen, and

R$^2$ is alkenyl or alkynyl.

12. The compound according to claim 11, wherein the compound is pyridine-2,5-dicarboxylic acid 2-allylamide 5-[(2-amino-phenyl)-amide].

13. The compound according to claim 9, wherein:

R$^1$ is hydrogen, and

R$^2$ is unsubstituted straight or branched $C_{1-12}$-alkyl or alkyl substituted by hydroxy, halogen, alkoxy, alkylsulfanyl, acyloxy, alkoxycarbonyl, acyl, $C_{1-6}$-alkyl-NH—C(O)—, or $C_{1-6}$-alkyl-C(O)NH—.

14. The compounds according to claim 13, wherein the compound is selected from pyridine-2,5-dicarboxylic acid 5-[(2-amino-phenyl)-amide]2-hexylamide, pyridine-2,5-dicarboxylic acid 5-[(2-amino-phenyl)-amide]2-[(2-methoxy-ethyl)-amide], pyridine-2,5-dicarboxylic acid 5-[(2-amino-phenyl)-amide]2-[(3-butoxy-propyl)-amide], {[5-(2-amino-phenylcarbamoyl)-pyridine-2-carbonyl]-amino}-acetic acid methyl ester, 3-{[5-(2-amino-phenylcarbamoyl)-pyridine-2-carbonyl]-amino}-propionic acid tert-butyl ester, pyridine-2,5-dicarboxylic acid 5-[(2-amino-phenyl)-amide]2-[(2,2,3,3,3-pentafluoro-propyl)-amide], pyridine-2,5-dicarboxylic acid 5-[(2-amino-phenyl)-amide]2-[(2,2,3,3,4,4,4-heptafluoro-butyl)-amide], pyridine-2,5-dicarboxylic acid 5-[(2-amino-phenyl)-amide]2-[(1,5-dimethyl-hexyl)-amide],
pyridine-2,5-dicarboxylic acid 5-[(2-amino-phenyl)-amide]2-[(1-methyl-hexyl)-amide], and
pyridine-2,5-dicarboxylic acid 2-[(2-acetylaminoethyl)-amide]5-[(2-amino-phenyl)-amide].

15. The compound according to claim 9, wherein:
$R^1$ is hydrogen, and
$R^2$ is alkyl substituted by —$NR^3R^4$, wherein $R^3$ and $R^4$ are each independently selected from hydrogen and $C_{1-6}$-alkyl.

16. The compound according to claim 15, wherein the compound is selected from
pyridine-2,5-dicarboxylic acid 5-[(2-amino-phenyl)-amide]2-[(2-diisopropylamino-ethyl)-amide], and
pyridine-2,5-dicarboxylic acid 5-[(2-amino-phenyl)-amide]2-[(3-dibutylamino-propyl)-amide].

17. The compound according to claim 9, wherein:
$R^1$ is hydrogen, and
$R^2$ is cycloalkyl.

18. The compound according to claim 17, wherein the compound is
pyridine-2,5-dicarboxylic acid 5-[(2-amino-phenyl)-amide]2-cyclooctylamide.

19. The compound according to claim 2, wherein Ar is pyridine-5,2-diyl, the compound having formula I-C

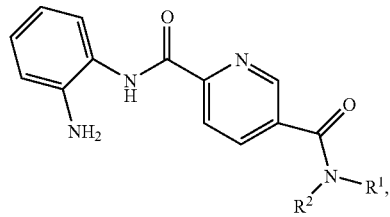

I-C wherein
$R^1$ is hydrogen or alkyl; and
$R^2$ is hydrogen, substituted or unsubstituted $C_{1-12}$-alkyl, substituted or unsubstituted $C_{2-12}$-alkenyl, or substituted or unsubstituted $C_{2-12}$-alkynyl, wherein the substituent is selected from hydroxy, halogen, alkoxy, alkylsulfanyl, acyloxy, alkoxycarbonyl, acyl, $C_{1-6}$-alkyl-NH—C(O)—, $C_{1-6}$-alkyl-C(O)NH— and —$NR^3R^4$.

20. The compound according to claim 19, wherein the compound is selected from
pyridine-2,5-dicarboxylic acid 2-[(2-amino-phenyl)-amide]5-(butyl-methyl-amide),
pyridine-2,5-dicarboxylic acid 5-(allyl-methyl-amide) 2-[(2-amino-phenyl)-amide],
pyridine-2,5-dicarboxylic acid 2-[(2-amino-phenyl)-amide]5-(methyl-prop-2-ynyl-amide),
pyridine-2,5-dicarboxylic acid 2-[(2-amino-phenyl)-amide]5-[bis-(2-methoxyethyl)-amide],
pyridine-2,5-dicarboxylic acid 2-[(2-amino-phenyl)-amide]5-(methyl-pentyl-amide),
pyridine-2,5-dicarboxylic acid 2-[(2-amino-phenyl)-amide]5-dipropylamide, and
pyridine-2,5-dicarboxylic acid 2-[(2-amino-phenyl)-amide]5-[(2-diethylaminoethyl)-methyl-amide].

21. The compound according to claim 19, wherein:
$R^1$ is hydrogen, and
$R^2$ is alkenyl or alkynyl.

22. The compound according to claim 21, wherein the compound is
pyridine-2,5-dicarboxylic acid 5-allylamide 2-[(2-amino-phenyl)-amide].

23. The compound according to claim 19, wherein:
$R^1$ is hydrogen, and
$R^2$ is unsubstituted alkyl or alkyl substituted by hydroxy, halogen, alkoxy, alkylsulfanyl, acyloxy, alkoxycarbonyl, acyl, $C_{1-6}$-alkyl-NH—C(O)—, or $C_{1-6}$-alkyl-C(O)NH—.

24. The compound according to claim 23, wherein the compound is selected from
pyridine-2,5-dicarboxylic acid 2-[(2-amino-phenyl)-amide]5-hexylamide,
pyridine-2,5-dicarboxylic acid 5-[(2-acetylamino-ethyl)-amide]2-[(2-amino-phenyl)-amide],
pyridine-2,5-dicarboxylic acid 2-[(2-amino-phenyl)-amide]5-[(2,2,3,3,3-pentafluoro-propyl)-amide],
pyridine-2,5-dicarboxylic acid 2-[(2-amino-phenyl)-amide]5-[(2,2,3,3,4,4,4-heptafluoro-butyl)-amide],
3-{[6-(2-amino-phenylcarbamoyl)-pyridine-3-carbonyl]-amino}-butyric acid ethyl ester,
pyridine-2,5-dicarboxylic acid 2-[(2-amino-phenyl)-amide]5-[(2-hydroxy-propyl)-amide],
2-{[6-(2-amino-phenylcarbamoyl)-pyridine-3-carbonyl]-amino}-3-methyl-butyric acid methyl ester,
3-{[6-(2-amino-phenylcarbamoyl)-pyridine-3-carbonyl]-amino}-propionic acid ethyl ester,
{[6-(2-amino-phenylcarbamoyl)-pyridine-3-carbonyl]-amino}-acetic acid methyl ester, and
pyridine-2,5-dicarboxylic acid 2-[(2-amino-phenyl)-amide]5-[(2-methoxy-ethyl)-amide].

25. The compound according to claim 23, wherein the compound is selected from
2-{[6-(2-amino-phenylcarbamoyl)-pyridine-3-carbonyl]-amino}-4-methylsulfanyl-butyric acid methyl ester,
3-{[6-(2-amino-phenylcarbamoyl)-pyridine-3-carbonyl]-amino}-propionic acid tert-butyl ester,
pyridine-2,5-dicarboxylic acid 2-[(2-amino-phenyl)-amide]5-[(2,3-dihydroxy-propyl)-amide],
pyridine-2,5-dicarboxylic acid 2-[(2-amino-phenyl)-amide]5-[(3-butoxy-propyl)-amide],
pyridine-2,5-dicarboxylic acid 2-[(2-amino-phenyl)-amide]5-sec-butylamide,
pyridine-2,5-dicarboxylic acid 2-[(2-amino-phenyl)-amide]5-[(1,5-dimethyl-hexyl)-amide], and
pyridine-2,5-dicarboxylic acid 2-[(2-amino-phenyl)-amide]5-[(1-methyl-hexyl)-amide].

26. The compound according to claim 19, wherein:
$R^1$ is hydrogen, and
$R^2$ is alkyl substituted by —$NR^3R^4$, wherein $R^3$ and $R^4$ are each independently selected from hydrogen and $C_{1-6}$-alkyl.

27. The compound according to claim 26, wherein the compound is selected from
pyridine-2,5-dicarboxylic acid 2-[(2-amino-phenyl)-amide]5-[(2-diisopropylamino-ethyl)-amide],
pyridine-2,5-dicarboxylic acid 2-[(2-amino-phenyl)-amide]5-[(2-dimethylamino-ethyl)-amide],
pyridine-2,5-dicarboxylic acid 2-[(2-amino-phenyl)-amide]5-[(4-diethylamino-1-methyl-butyl)-amide], and
pyridine-2,5-dicarboxylic acid 2-[(2-amino-phenyl)-amide]5-[(3-dibutylamino-propyl)-amide].

28. The compound according to claim 19, wherein:
$R^1$ is hydrogen or alkyl, and
$R^2$ is cycloalkyl.

29. The compound according to claim 26, wherein the compound is selected from
pyridine-2,5-dicarboxylic acid 2-[(2-amino-phenyl)-amide]5-cyclooctylamide, and
pyridine-2,5-dicarboxylic acid 2-[(2-amino-phenyl)-amide]5-(cyclopropylmethyl-propyl-amide).

30. The compound according to claim 1, of the formula I-E

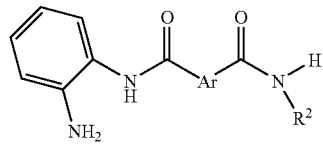

wherein,
Ar is pyridine-2,5-diyl, pyridine-2,6-diyl, pyridine-2,4-diyl, or pyridine-5,2-diyl; and
$R^2$ represents hydroxy, alkoxy, $C_2$–$C_{12}$-alkenyloxy or phenoxy.

31. The compound according to claim 30, wherein the compound is selected from
pyridine-2,5-dicarboxylic acid 2-[(2-amino-phenyl)-amide]5-hydroxyamide,
pyridine-2,5-dicarboxylic acid 5-[(2-amino-phenyl)-amide]2-hydroxyamide,
pyridine-2,6-dicarboxylic acid 2-[(2-amino-phenyl)-amide]6-hydroxyamide, and
pyridine-2,4-dicarboxylic acid 2-[(2-amino-phenyl)-amide]4-hydroxyamide.

32. The compound according to claim 1, wherein the compound is selected from
pyridine-2,5-dicarboxylic acid 2-(allyl-cyclopentyl-amide) 5-[(2-amino-phenyl)-amide],
pyridine-2,5-dicarboxylic acid 5-[(2-amino-phenyl)-amide]2-(cyclopropylmethyl-propyl-amide),
pyridine-2,5-dicarboxylic acid 5-[(2-amino-phenyl)-amide]2-sec-butylamide,
pyridine-2,5-dicarboxylic acid 2-[(2-amino-phenyl)-amide]5-[(2-hydroxy-ethyl)-amide],
pyridine-2,5-dicarboxylic acid 2-[(2-amino-phenyl)-amide]5-{[2-(2-hydroxy-ethoxy)-ethyl]-amide}, and
pyridine-2,5-dicarboxylic acid 2-[(2-amino-phenyl)-amide]5-[(cyclohexylmethyl-2-hydroxy-ethyl)-amide].

33. The compound according to claim 1, wherein the compound is selected from
pyridine-2,5-dicarboxylic acid 2-[(2-amino-phenyl)-amide]5-[(4-hydroxy-butyl)-amide],
pyridine-2,5-dicarboxylic acid 2-[(2-amino-phenyl)-amide]5-[(1-hydroxymethyl-2-methyl-butyl)-amide],
pyridine-2,5-dicarboxylic acid 2-[(2-amino-phenyl)-amide]5-[(4-hydroxy-cyclohexyl)-amide],
pyridine-2,5-dicarboxylic acid 2-[(2-amino-phenyl)-amide]5-({2-[bis-(2-hydroxy-ethyl)-amino]-ethyl}-amide),
pyridine-2,5-dicarboxylic acid 5-[(2-amino-phenyl)-amide]2-[(2-dimethylamino-ethyl)-amide] and
pyridine-2,5-dicarboxylic acid 2-[(2-amino-phenyl)-amide]5-[(2-dimethylamino-ethyl)-ethyl-amide].

34. A process for the preparation of a compound of formula I

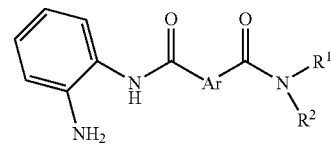

wherein
Ar is pyridine-2,5-diyl, pyridine-5,2-diyl, pyridine-2,6-diyl, or pyridine-2,4-diyl,
$R^1$, $R^2$ are each independently selected from hydrogen, substituted or unsubstituted $C_{1-12}$-alkyl, substituted or unsubstituted $C_{2-12}$-alkenyl, substituted or unsubstituted $C_{2-12}$-alkynyl, and substituted or unsubstituted $C_{3-12}$-cycloalkyl, wherein the substituent is selected from hydroxy, halogen, $C_{3-12}$-cycloalklyl, alkoxy, alkylsulfanyl, acyloxy, alkoxycarbonyl, acyl, $C_{1-6}$-alkyl-NH—C(O)—, $C_{1-6}$-alkyl-C(O)NH— and —$NR^3R^4$, or alternatively
$R^1$ is hydrogen, and
$R^2$ is hydroxy, alkoxy, $C_2$–$C_{12}$-alkenyloxy, phenoxy, or phenoxy substituted with methyl, methoxy, halogen, nitro, cyano, trifluoromethyl, ethenyl or —C(O)—O—$CH_3$; and
$R^3$ and $R^4$ are each independently selected from hydrogen or $C_{1-6}$-alkyl, or alternatively
$R^3$ and $R^4$ together with the nitrogen-atom to which they are attached form a ring, which ring is monosubstituted by oxo and which ring optionally contains a further heteroatom,
or a pharmaceutically acceptable salt thereof, comprising:
activating a compound of the formula II

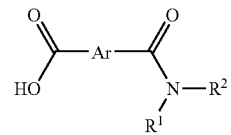

wherein when R2 is hydroxy, $R^2$ the hydroxyl is optionally protected by a protecting group,
in the presence of an activating agent;
adding a compound of formula III

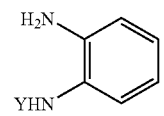

wherein Y represents hydrogen or a suitable amino protecting group; and cleaving off any protecting groups to give a compound of formula I.

35. The process according to claim 34, further comprising adding at least one of an acid and a base to form a pharmaceutically acceptable salt.

36. A process for the preparation of a compound of formula I

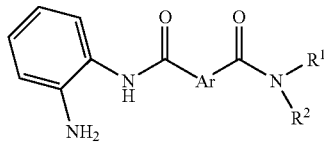

wherein

Ar is pyridine-2,5-diyl, pyridine-5,2-diyl, pyridine-2,6-diyl, or pyridine-2,4-diyl, $R^1$, $R^2$ are each independently selected from hydrogen, substituted or unsubstituted $C_{1-12}$-alkyl, substituted or unsubstituted $C_{2-12}$-alkenyl, substituted or unsubstituted $C_{2-12}$-alkynyl, and substituted or unsubstituted $C_{3-12}$-cycloalkyl, wherein the substituent is selected from hydroxy, halogen, $C_{3-12}$-cycloalkyl, alkoxy, alkylsulfanyl, acyloxy, alkoxycarbonyl, acyl, $C_{1-6}$-alkyl-NH—C(O)—, $C_{1-6}$-alkyl-C(O)NH— and —$NR^3R^4$, or alternatively $R^1$ is hydrogen, and $R^2$ is hydroxy, alkoxy, $C_2$–$C_{12}$-alkenyloxy, phenoxy, or phenoxy substituted with methyl, methoxy, halogen, nitro, cyano, trifluoromethyl, ethenyl or —C(O)—O—$CH_3$; and $R^3$ and $R^4$ are each independently selected from hydrogen or $C_{1-6}$-alkyl, or alternatively $R^3$ and $R^4$ together with the nitrogen-atom to which they are attached form a ring, which ring is monosubstituted by oxo and which ring optionally contains a further heteroatom, or a pharmaceutically acceptable salt thereof, comprising:

reacting a compound of the formula VI

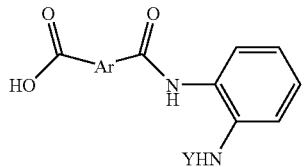

wherein Y is suitable protecting group, with an an amine of the formula $HNR^1R^2$, and wherein when $R^2$ is hydroxy, the hydroxyl optionally is protected wth a protecting group; and cleaving off any protecting groups to give a compound of formula I.

37. The process according to claim 36, further comprising adding at least one of an acid and a base to form a pharmaceutically acceptable salt.

38. A pharmaceutical composition comprising:

a compound according to claim 1; and a pharmaceutically acceptable carrier or excipient.

39. A method of treating cancer, comprising administering, to a patient in need thereof, a therapeutically effective amount of a compound according to claim 1.

* * * * *

UNITED STATES PATENT AND TRADEMARK OFFICE
CERTIFICATE OF CORRECTION

| | | |
|---|---|---|
| PATENT NO. | : 7,071,219 B2 | Page 1 of 1 |
| APPLICATION NO. | : 10/771184 | |
| DATED | : July 4, 2006 | |
| INVENTOR(S) | : Georg Fertig et al. | |

It is certified that error appears in the above-identified patent and that said Letters Patent is hereby corrected as shown below:

In the Title Page, insert item (30) "Foreign Application Priority Data"

February 6, 2003, Europe, No. 03002545.6
April 8, 2003, Europe, No. 03016692.0

Signed and Sealed this

Twenty-ninth Day of July, 2008

JON W. DUDAS
*Director of the United States Patent and Trademark Office*